United States Patent
Suzuki et al.

(10) Patent No.: US 7,510,781 B2
(45) Date of Patent: Mar. 31, 2009

(54) SPIRO COMPOUND AND ORGANIC LUMINESCENCE DEVICE USING THE SAME

(75) Inventors: Koichi Suzuki, Yokohama (JP); Mizuho Hiraoki, Kawasaki (JP); Akihiro Senoo, Kawasaki (JP); Naoki Yamada, Komae (JP); Chika Negishi, Kawasaki (JP); Akihito Saito, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 259 days.

(21) Appl. No.: 10/525,327

(22) PCT Filed: Aug. 12, 2003

(86) PCT No.: PCT/JP03/10258

§ 371 (c)(1),
(2), (4) Date: Feb. 22, 2005

(87) PCT Pub. No.: WO2004/020373

PCT Pub. Date: Mar. 11, 2004

(65) Prior Publication Data

US 2006/0134425 A1 Jun. 22, 2006

(30) Foreign Application Priority Data

Aug. 27, 2002 (JP) ............................. 2002-246601

(51) Int. Cl.
*H01L 51/54* (2006.01)
*H05B 33/14* (2006.01)
*C07F 7/08* (2006.01)

(52) U.S. Cl. ...................... 428/690; 428/917; 313/504; 313/506; 546/16; 556/406

(58) Field of Classification Search ................. 428/690, 428/917; 257/40; 313/504, 506; 546/406, 546/16; 556/406
See application file for complete search history.

(56) References Cited

U.S. PATENT DOCUMENTS 4,539,507 A 9/1985 Van Slyke et al. ........... 313/504

(Continued)

FOREIGN PATENT DOCUMENTS

CN 1170425 11/1995

(Continued)

OTHER PUBLICATIONS

Ari Auram, "Molecule for memory, Logic, and Amplification"; J. Am. Chem. Soc. 110(17) 5687-5692 (1998).

(Continued)

*Primary Examiner*—D. Lawrence Tarazano
*Assistant Examiner*—Camie S Thompson
(74) *Attorney, Agent, or Firm*—Fitzpatrick, Cella, Harper & Scinto

(57) ABSTRACT

Provided are a novel spiro compound, and an organic luminescence device using the spiro compound and having an optical output with an extremely high efficiency and a high luminance, and an extremely high durability. The Spiro compound is represented by the following general formula [I]:

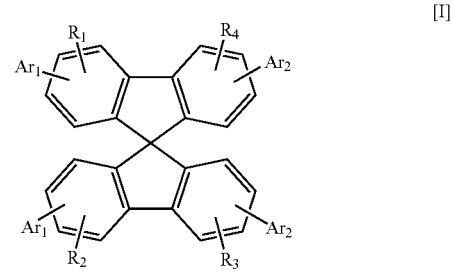

(wherein $R_1$, $R_2$, $R_3$, and $R_4$ represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom, and $R_1$, $R_2$, $R_3$, and $R_4$ may be identical or different from each other; and $Ar_1$ and $Ar_2$ represent a substituted or unsubstituted condensed polycyclic aromatic group or a substituted or unsubstituted condensed polycyclic heterocyclic group, which may be identical or different from each other.)

2 Claims, 3 Drawing Sheets

U.S. PATENT DOCUMENTS

| | | | | |
|---|---|---|---|---|
| 4,720,432 | A | 1/1988 | Van Slyke et al. | 428/457 |
| 4,885,211 | A | 12/1989 | Tang et al. | 428/457 |
| 5,130,603 | A | 7/1992 | Tokailin et al. | 313/504 |
| 5,151,629 | A | 9/1992 | Van Slyke | 313/504 |
| 5,227,252 | A | 7/1993 | Murayama et al. | 428/690 |
| 5,247,190 | A | 9/1993 | Friend et al. | 257/40 |
| 5,317,169 | A | 5/1994 | Nakano et al. | 257/40 |
| 5,382,477 | A | 1/1995 | Saito et al. | 428/690 |
| 5,409,783 | A | 4/1995 | Tang et al. | 428/690 |
| 5,514,878 | A | 5/1996 | Holmes et al. | 257/40 |
| 5,672,678 | A | 9/1997 | Holmes et al. | 528/373 |
| 5,726,457 | A | 3/1998 | Nakano et al. | 257/40 |
| 5,840,217 | A | 11/1998 | Zupo et al. | 252/583 |
| 6,093,864 | A | 7/2000 | Tokailin et al. | 585/25 |
| 6,329,082 | B1 | 12/2001 | Kreuder et al. | 428/690 |
| 6,416,887 | B1* | 7/2002 | Tokito et al. | 428/690 |
| 6,652,997 | B2 | 11/2003 | Suzuki et al. | 428/690 |
| 6,916,552 | B2* | 7/2005 | Ueda et al. | 428/690 |
| 6,916,555 | B2 | 7/2005 | Suzuki et al. | 428/690 |
| 2003/0235713 | A1 | 12/2003 | Suzuki et al. | 428/690 |
| 2004/0253389 | A1 | 12/2004 | Suzuki et al. | 428/1.1 |
| 2004/0263067 | A1 | 12/2004 | Saitoh et al. | 313/504 |
| 2004/0265632 | A1 | 12/2004 | Okinaka et al. | 428/690 |
| 2005/0106414 | A1 | 5/2005 | Saitoh et al. | 428/690 |
| 2006/0068221 | A1* | 3/2006 | Saitoh et al. | 428/690 |

FOREIGN PATENT DOCUMENTS

| | | | |
|---|---|---|---|
| EP | DE 44/42050 A1 | 11/1994 | |
| EP | 1341403 | 11/2001 | |
| ES | 2125056 | 11/1995 | |
| JP | 02-247278 | 10/1990 | |
| JP | 03-255190 | 11/1991 | |
| JP | 04-145192 | 5/1992 | |
| JP | 05-202356 | 8/1993 | |
| JP | 05-247460 | 9/1993 | |
| JP | 07-278537 | 10/1995 | |
| JP | 09-202878 | 8/1997 | |
| JP | 09-227576 | 9/1997 | |
| JP | 10-509996 | 9/1998 | |
| JP | 2002-75645 | 3/2002 | |
| JP | 2002-222697 | 8/2002 | |
| WO | WO 02/43449 A1 | 11/2001 | |
| WO | WO 96/17035 | 11/2001 | |

OTHER PUBLICATIONS

Burroughes, et al; "Light-emitting diodes based on Conjugated polymers"; Nature, 347, 539-541 (1990).

Miyaura, et al; Palladium-Catalyzed Cross-Coupling Reactions of Organoboron Compounds, Chem. Rev. 95, (7), 2457-2483 (1995).

Wu, et al; "Convergent Syntheic Routes to Orthogonally Fused Conjugated Oligomers Directed toward Molecular Scale Electronic Device Applications"; J. Org. Chem. 61 (20) 6906-6921 (1996).

Baldo, et al; Highly efficient phosphorescent emission from organic electroluminescent devices; Nature, 395 (6698) 151-154 (1998).

Yamamoto, et al; "A Novel Type of Polycondensation Utilizing Transition Metal-Catalyzed C-C Coupling"; Bulletin of The Chemical Society of Japan; vol. 51; No. 7; pp. 2091-2097 (1978).

Ghosal, et al; "Formation of the 1,3-Dienes, and Biphenyls via the copper (II) Nitrate Mediated Coupling of Organotin compounds"; J. Org. Chem., vol. 52, No. 19, pp. 4296-4298 (1987).

Tang, et al; "Organic Electroluminrscent diodes"; Appl. Phys. Lett. 51 (12) 913-915 (1987).

* cited by examiner

SPIRO COMPOUND AND ORGANIC LUMINESCENCE DEVICE USING THE SAME

TECHNICAL FIELD

The present invention relates to a novel organic compound and an organic luminescence device using the same.

BACKGROUND ART

An organic luminescence device is a device where a thin film including a fluorescent organic compound or a phosphorescent organic compound is sandwiched between an anode and a cathode, an electron and a hole are injected from the respective electrodes to generate an exciton of the fluorescent compound or the phosphorescent compound, and light which is emitted when the exciton returns to the ground state is utilized.

According to the study of Kodak company in 1987 (Appl. Phys. Lett. 51, 913 (1987)), there has been reported a luminescence with approximately 1000 cd/m² at an applied voltage of approximately 10 V in a device having a separated-function type two-layer configuration using ITO as an anode, a magnesium-silver alloy as a cathode, an aluminum quinolinol complex as an electron-transporting material and a luminescent material, and a triphenyl amine derivative as a hole-transporting material. The related patents include U.S. Pat. Nos. 4,539,507, 4,720,432, 4,885,211, and so on.

In addition, it is possible to generate luminescence in the range of ultraviolet to infrared lights by changing the type of the fluorescent organic compound, and in recent years various types of compounds have been studied actively. For instance, it is described in U.S. Pat. Nos. 5,151,629, 5,409,783, 5,382,477, Japanese Patent Application Laid-Open Nos. 2-247278, 3-255190, 5-202356, 9-202878, 9-227576, and so on.

In recent years, many studies have been conducted using phosphorescent compounds as luminescent materials and using energies in triplet excitation states. A high luminescence efficiency shown by an organic luminescence device using an iridium complex as a luminescent material has been reported by a group of the Princeton University (Nature 395, 151 (1998)).

Furthermore, in addition to the organic luminescence device using the low molecular weight material as mentioned above, an organic luminescence device using a conjugate polymer has been reported by a group of the Cambridge University (Nature, 347, 539 (1990)). In this report, luminescence from a single layer is confirmed by the film formation of polyphenylene vinylene (PPV) using a coating system.

The related patents of the organic luminescence device using the conjugate polymer include U.S. Pat. Nos. 5,247,190, 5,514,878, 5,672,678, Japanese Patent Application Laid-Open Nos. 4-145192, 5-247460, and so on.

In this way, the recent progress in the organic luminescence device is remarkable, and the characteristics thereof suggest the possibility of applications for various purposes, which enable the luminescence device with a high luminance, a high-speed response, and a thin and lightweight form.

However, an optical output of higher luminance or higher conversion efficiency is required under the present conditions. In addition, many problems still remain to be solved regarding the durability with respect to a change with time due to a long-term usage, deterioration caused by an atmospheric gas including oxygen, moisture, or the like, and so on. Besides, it is not still insufficient for solving problems related to the needs for luminescences of blue, green, and red having good color purity in the case of considering the applications to a full color display and so on.

On the other hand, a spiro compound having a specific steric configuration has been attracting attention as an organic functional material in terms of the specific physical properties of the material (J. Am. Chem. Soc., vol. 110, page 5687, 1988). As an example of using a spiro compound as an organic luminescence device, Japanese Patent Application Laid-Open No. 7-278537 or the like can be given, but the characteristics thereof in being used as a luminescent material or an electron-transporting material are not sufficient.

DISCLOSURE OF THE INVENTION

An object of the present invention is to provide a novel spiro compound.

Also, another object of the present invention is to provide an organic luminescence device using a specific spiro compound and having an optical output with an extremely high efficiency and a high luminance.

In addition, another object of the present invention is to provide an organic luminescence device having an extremely high durability. Furthermore, another object of the present invention is to provide an organic luminescence device which can be easily and comparatively inexpensively produced.

Therefore, a spiro compound according to the present invention is represented by one of the following general formula [I] and [II]:

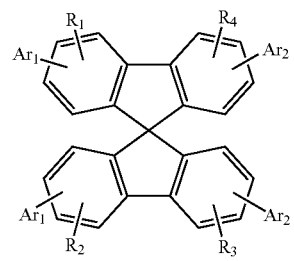

[I]

(where $R_1$, $R_2$, $R_3$, and $R_4$ represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom, and $R_1$, $R_2$, $R_3$, and $R_4$ may be identical or different from each other; and $Ar_1$ and $Ar_2$ represent a substituted or unsubstituted condensed polycyclic aromatic group or a substituted or unsubstituted condensed polycyclic heterocyclic group, which may be identical or different from each other); and

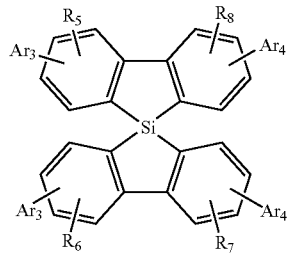

[II]

(where $R_5$, $R_6$, $R_7$, and $R_8$ represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom, and $R_5$, $R_6$, $R_7$, and $R_8$ may be identical or different from each other; and Ar₃ and Ar₄ represent a substituted or unsubstituted condensed polycyclic aromatic group or a substituted or unsubstituted condensed polycyclic heterocyclic group, which may be identical or different from each other.)

Further, an organic luminescence device according to the present invention includes at least a pair of electrodes including an anode and a cathode and one or a plurality of layers containing an organic compound sandwiched between the pair of electrodes, in which at least one of the layers containing the organic compound preferably contains at least one spiro compound.

BEST MODE FOR CARRYING OUT THE INVENTION

Figure 1:
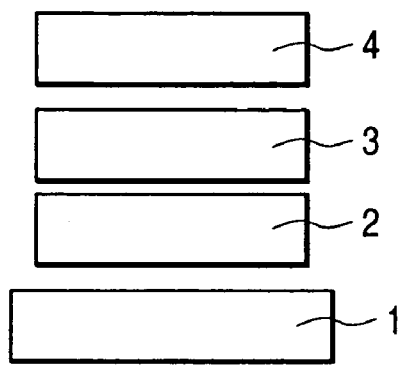
FIG. 1 is a cross-sectional diagram that illustrates an example of an organic luminescence device in accordance with the present invention.

Hereinafter, the present invention will be described in detail.

At first, a spiro compound of the present invention will be described.

The spiro compound of the present invention is represented by the above general formula [I] or [II].

Here, at least one of $Ar_1$ and $Ar_2$, or at least one of $Ar_3$ and $Ar_4$ is preferably a condensed polycyclic aromatic group represented by one of the following general formula [III] to [IX]:

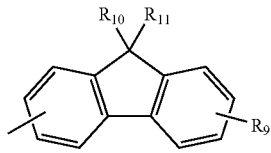

[III]

(where $R_9$ represents a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom; and $R_{10}$ and $R_{11}$ represent a hydrogen atom, a substituted or unsubstituted alkyl group, a substituted or unsubstituted aralkyl group, a substituted or unsubstituted aryl group, or a substituted or unsubstituted heterocyclic group, which may be identical or different from each other);

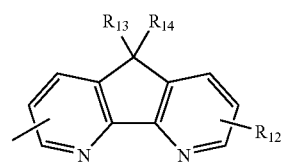

[IV]

(where $R_{12}$ represents a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom; and $R_{13}$ and $R_{14}$ represent a hydrogen atom, a substituted or unsubstituted alkyl group, a substituted or unsubstituted aralkyl group, a substituted or unsubstituted aryl group, or a substituted or unsubstituted heterocyclic group, which may be identical or different from each other); and

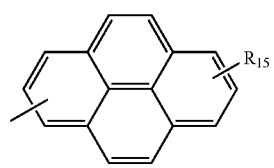

[V]

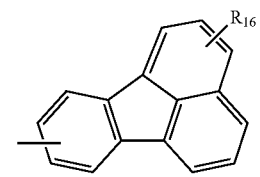

[VI]

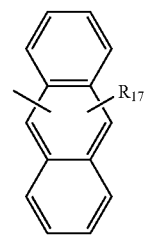

[VII]

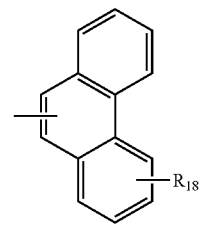

[VIII]

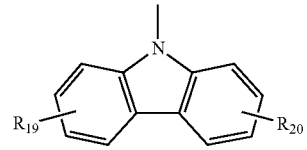

[IX]

(where $R_{15}$ to $R_{20}$ represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom.)

Specific examples of substituents in the above general formula [I] to [IX] are shown below.

The alkyl group includes a methyl group, an ethyl group, an n-propyl group, an iso-propyl group, an n-butyl group, a tert-butyl group, an octyl group, and the like.

The aralkyl group includes a benzyl group, a phenethyl group, and the like.

The aryl group includes a phenyl group, a biphenyl group, a tert-phenyl group, and the like.

The heterocyclic group includes a thienyl group, a pyrrolyl group, a pyridyl group, an oxazolyl group, an oxadiazolyl group, a thiazolyl group, a thiadiazolyl group, a tert-thienyl group, and the like.

The substituted amino group includes a dimethylamino group, a diethylamino group, a dibenzylamino group, a diphenylamino group, a ditolylamino group, a dianisolylamino group, and the like.

The halogen atom includes fluorine, chlorine, bromine, iodine, and the like.

The condensed polycyclic aromatic group includes a fluorenyl group, a naphthyl group, a fluoranthenyl group, an anthryl group, a phenanthryl group, a pyrenyl group, a tetracenyl group, a pentacenyl group, a triphenylenyl group, a perylenyl group, and the like.

The condensed polycyclic heterocyclic group includes a carbazolyl group, a diazafluorenyl group, an acridinyl group, and the like.

The substituents which the above-mentioned substituents may have include alkyl groups such as a methyl group, an ethyl group, and a propyl group; aralkyl groups such as a benzyl group, and a phenethyl group; aryl groups such as a phenyl group, and a biphenyl group; heterocyclic groups such as a thienyl group, a pyrrolyl group, and a pyridyl group; amino groups such as a dimethylamino group, a diethylamino group, a dibenzylamino group, a diphenylamino group, a ditolylamino group, and a dianisolylamino group; alkoxyl groups such as a methoxyl group, an ethoxyl group, a propoxyl group, and a phenoxyl group; a cyano group; halogen atoms such as fluorine, chlorine, bromine, and iodine; and the like.

Next, although a typical example of the spiro compound of the present invention will be hereinafter given, the present invention is not limited thereto.

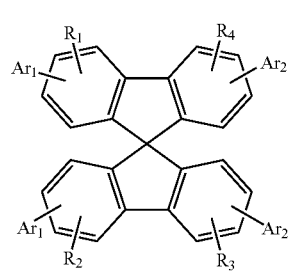

[I]

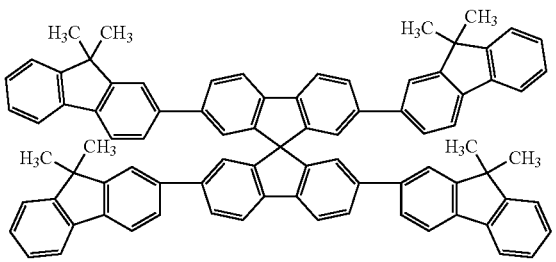

1

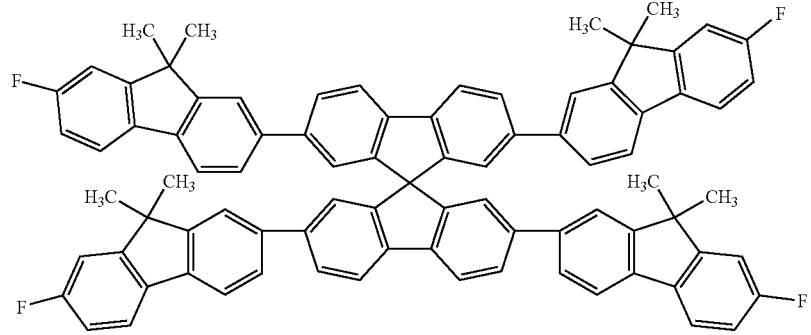

2

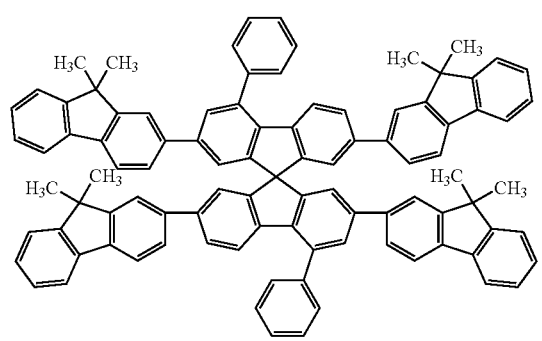

3

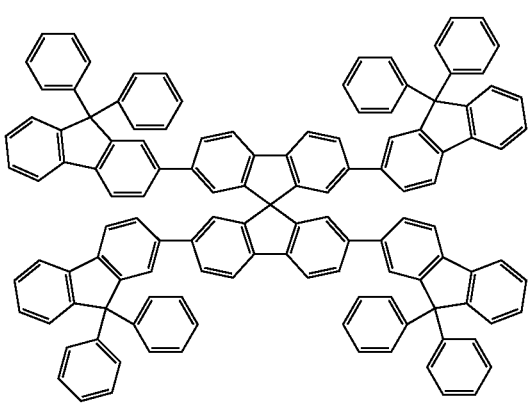

4

-continued
| 5 | 6 |
|---|---|
| 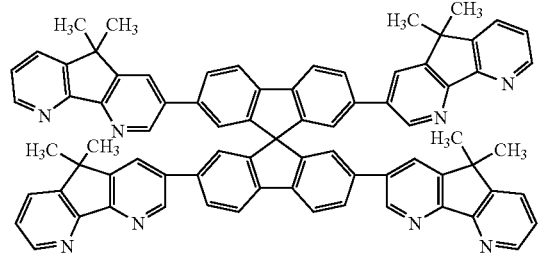 | 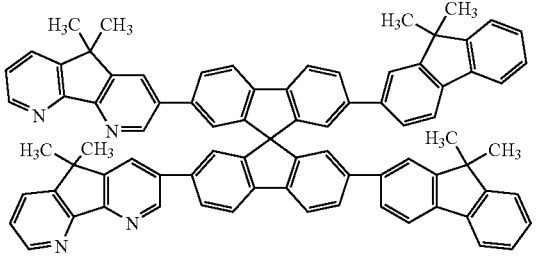 |
| 7 | 8 |
| 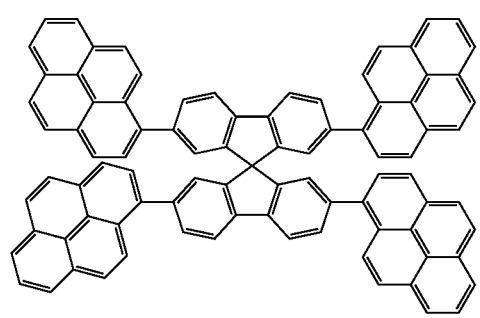 | 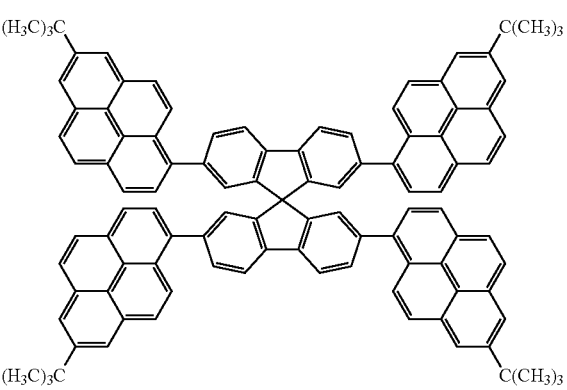 |
| 9 | 10 |
| 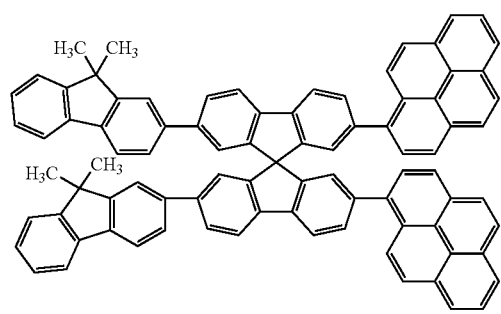 | 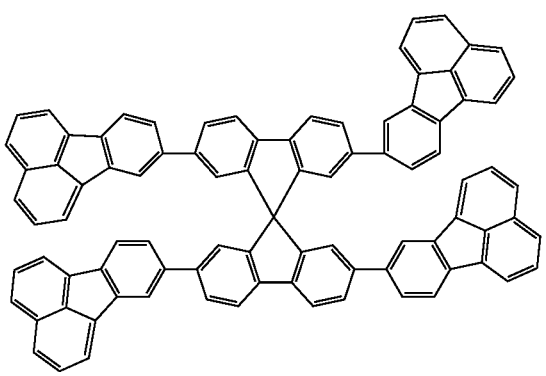 |
| 11 | 12 |
| 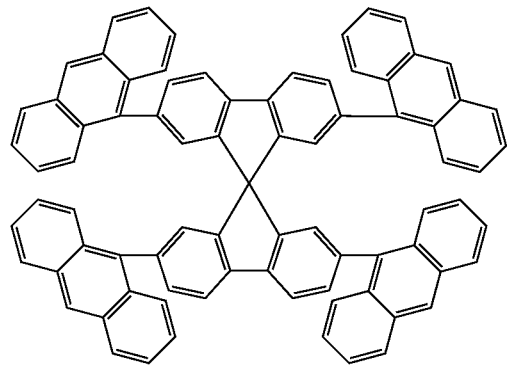 | 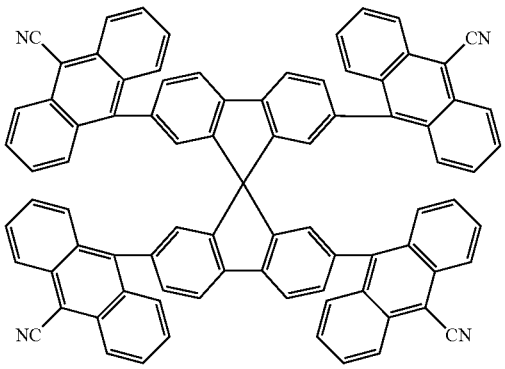 |

-continued
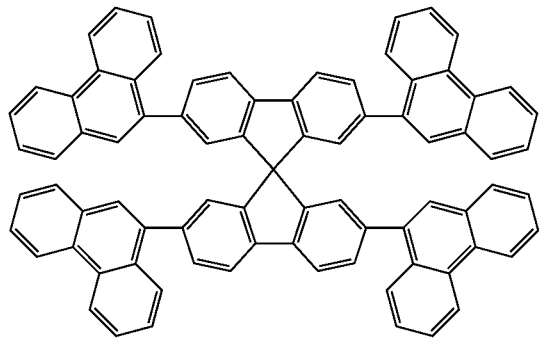
13
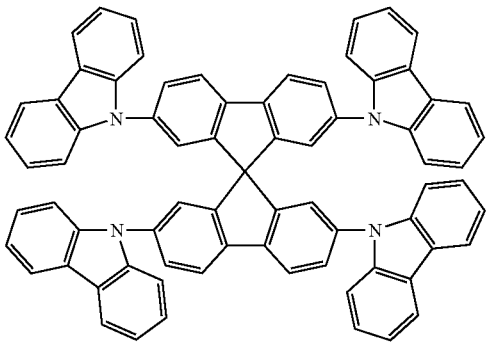
14
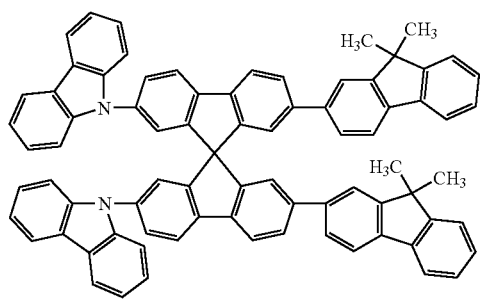
15
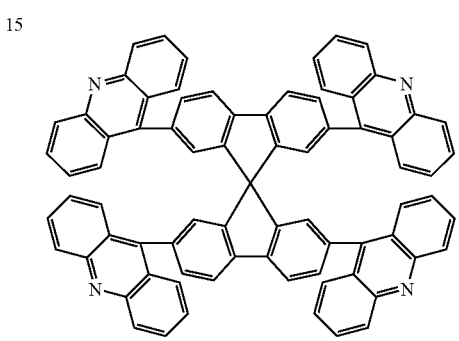
16
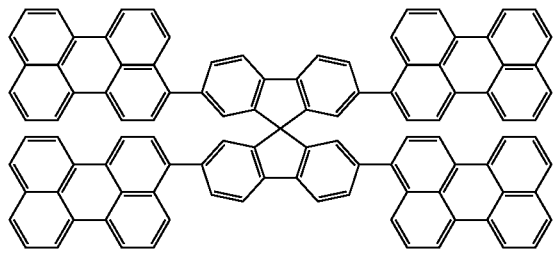
17
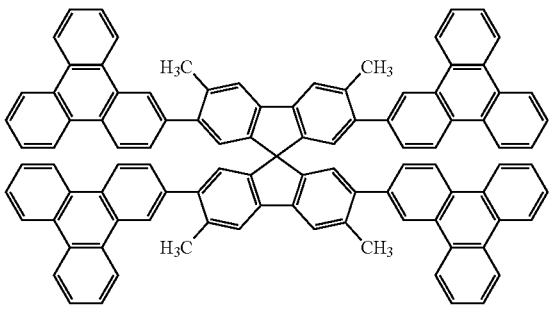
18
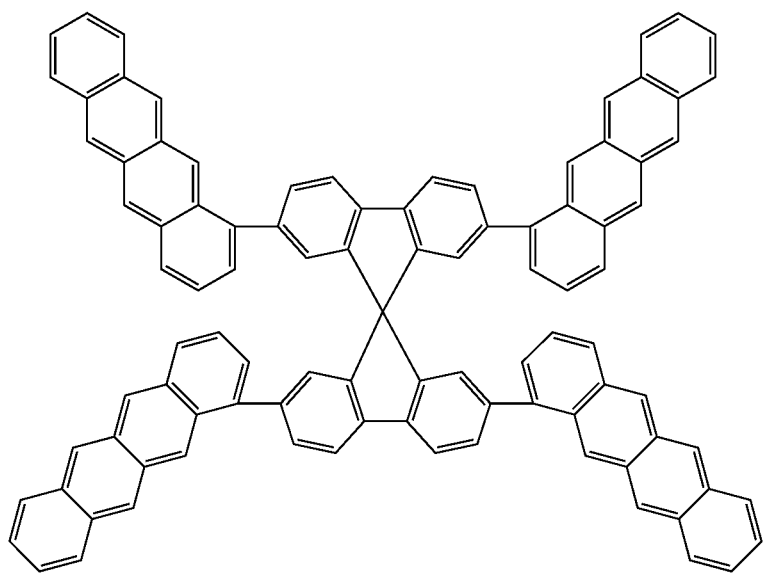
19

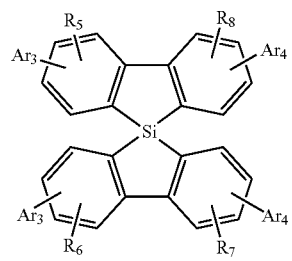
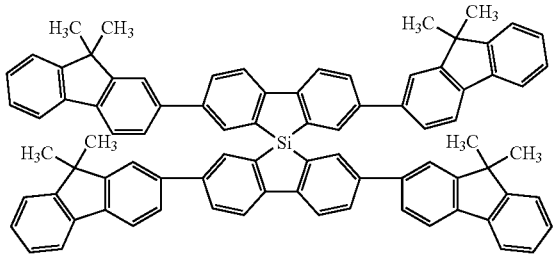
[II]
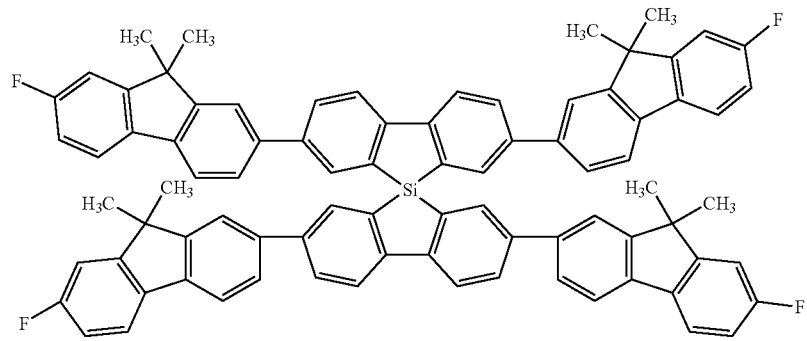
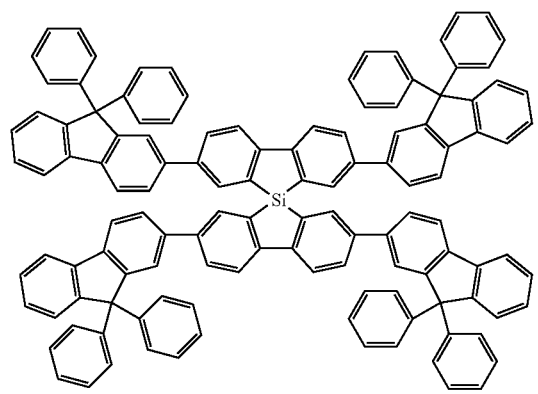
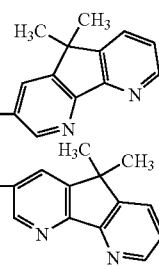
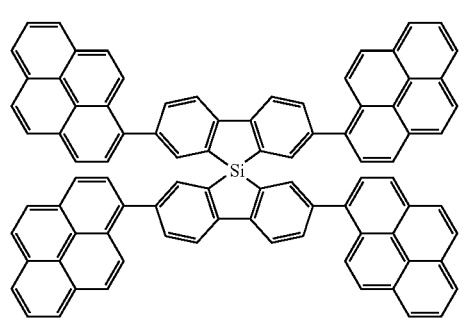
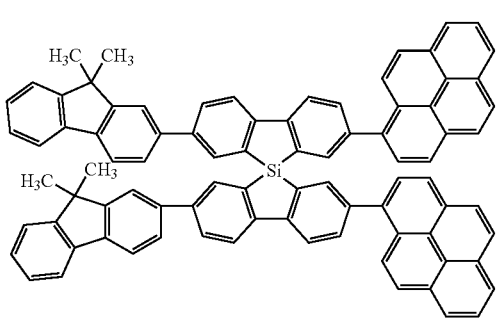

-continued
26
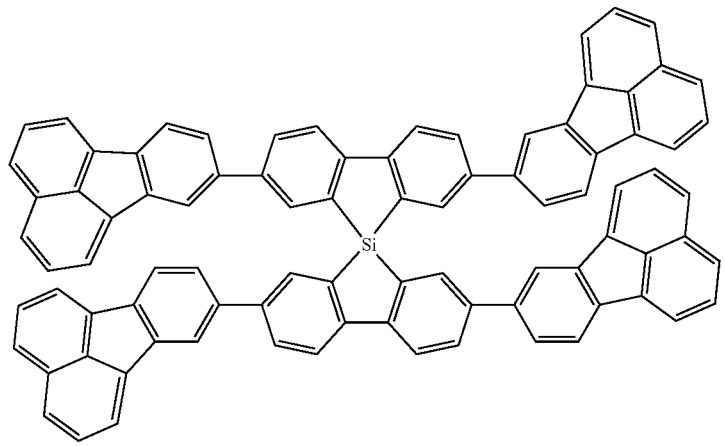
27
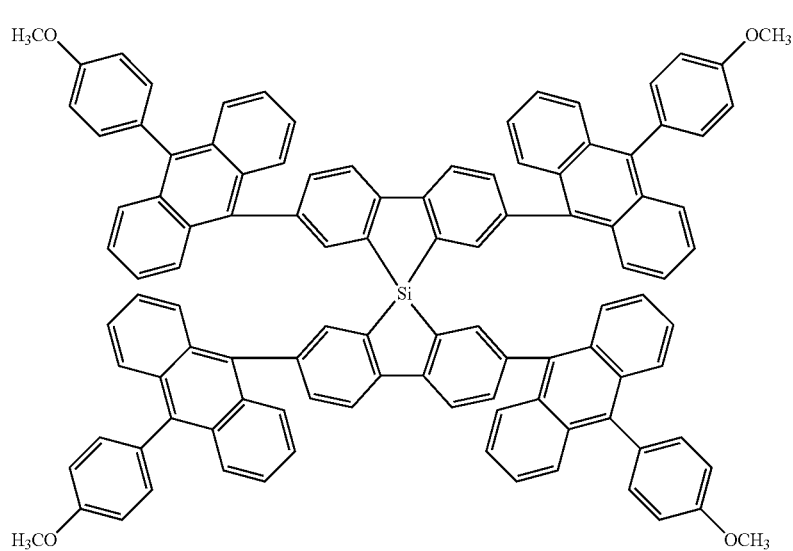
28
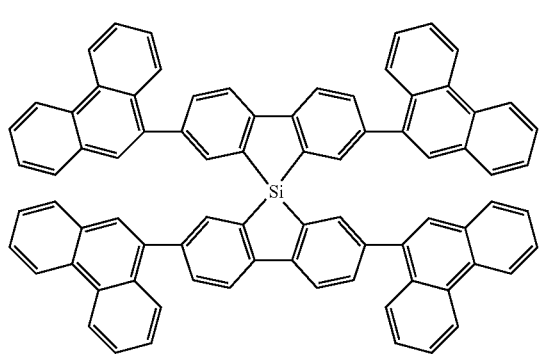
29
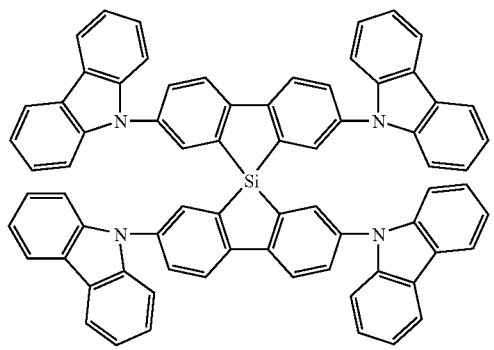

-continued

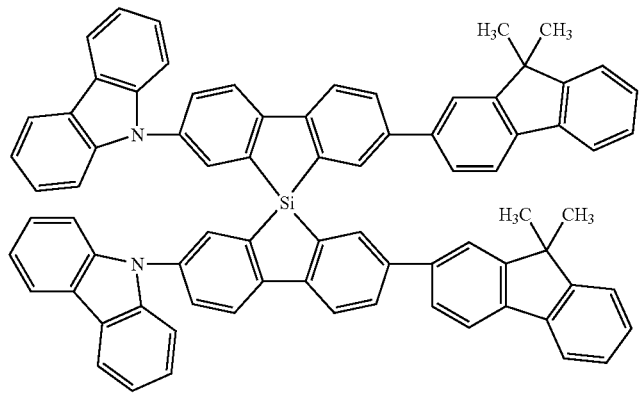

The Spiro compound of the present invention can be synthesized by a generally well-known method, for example an intermediate of the spiro compound is obtained by a method described in J. Org. Chem., 61, 6906, 1996, J. Am. Chem. Soc., 80, 1883, 1958, or the like, and furthermore the intermediate can be synthesized by the suzuki coupling method (e.g., Chem. Rev. 1995, 95, 2457-2483) using a palladium catalyst, the Yamamoto method (e.g., Bull. Chem. Soc. Jpn. 51, 2091, 1978) using a nickel catalyst, a method in which a synthesis is performed by using a tin aryl compound (e.g., J. Org. Chem., 52, 4296, 1987), and so on.

As compared with the conventional compound, the spiro compound of the present invention is a compound having excellent electron-transporting property, luminescence property and durability, which is useful for organic compound-containing layers of an organic luminescence device, particularly an electron-transporting layer and a luminescent layer, and a layer formed by a vacuum evaporation method, a solution-coating method, or the like hardly causes crystallization or the like and is excellent in stability with time.

Next, the organic luminescence device of the present invention will be described in detail.

The organic luminescence device of the present invention includes at least a pair of electrodes including an anode and a cathode and one or plural organic compound-containing layers sandwiched between the pair of electrodes, in which at least one layer of the organic compound-containing layers contains at least one spiro compound represented by the above general formula [I] or the general formula [II].

In the organic luminescence device of the present invention, it is preferable that at least an electron-transporting layer or a luminescent layer among the organic-compound-containing layers contain at least one Spiro compound.

In the organic luminescence device of the present invention, the spiro compound represented by the above general formula [I] or the general formula [II] is formed between the anode and the cathode by the vacuum evaporation method or the solution-coating method. The thickness of the organic layer is smaller than 10 μm, and it is preferable to make the layer as a thin film with a thickness of preferably 0.5 μm or less, more preferably 0.01 to 0.5 μm.

Further, according to a preferable mode of the organic luminescence device of the present invention, at least a luminescent layer among the layers containing the organic compound includes at least one spiro compound and a fluorene compound represented by one of the following general formula [X] and [XI]:

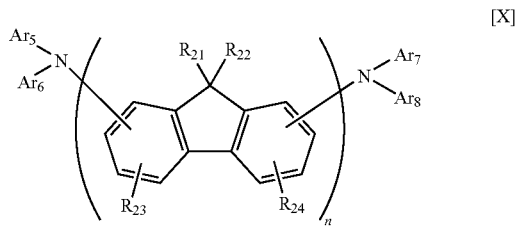

[X]

(where $R_{21}$ and $R_{22}$ represent a hydrogen atom, a substituted or unsubstituted alkyl group, a substituted or unsubstituted aralkyl group, a substituted or unsubstituted aryl group, or a substituted or unsubstituted heterocyclic group, $R_{21}$, themselves or $R_{22}$ themselves, which are bonded to different fluorene groups, may be identical or different from each other, and $R_{21}$ and $R_{22}$ that are bonded to the same fluorene group may be identical or different from each other; $R_{23}$ and $R_{24}$ represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen atom, and $R_{23}$ themselves or $R_{24}$ themselves, which are bonded to different fluorene groups, may be identical or different from each other, and $R_{23}$ and $R_{24}$ that are bonded to the same fluorene group may be identical or different from each other; $Ar_5$, $Ar_6$, $Ar_7$, and $Ar_8$ represent a substituted or unsubstituted aromatic group, a substituted or unsubstituted heterocyclic group, a substituted or unsubstituted condensed polycyclic aromatic group, or a substituted or unsubstituted condensed polycyclic heterocyclic group, which may be identical or different from each other, and $Ar_5$ and $Ar_6$ as well as $Ar_7$ and $Ar_8$ may be bonded with each other to form rings, respectively; and n represents an integral number of 1 to 10); and

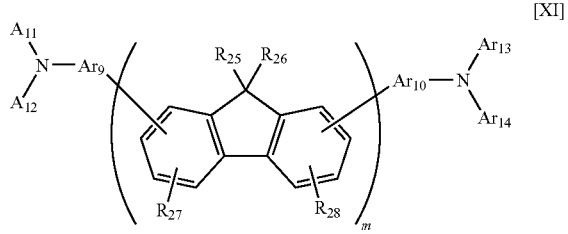

[XI]

(where $R_{25}$ and $R_{26}$ represent a hydrogen atom, a substituted or unsubstituted alkyl group, a substituted or unsubstituted aralkyl group, a substituted or unsubstituted aryl group, or a substituted or unsubstituted heterocyclic group, $R_{25}$ themselves or $R_{26}$ themselves, which are bonded to different fluorene groups, may be identical or different from each other, and $R_{25}$ and $R_{26}$ that are bonded to the same fluorene group may be identical or different from each other; $R_{27}$ and $R_{28}$ represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen atom, and $R_{27}$ themselves or $R_{28}$ themselves, which are bonded to different fluorene groups, may be identical or different from each other, and $R_{27}$ and $R_{28}$ that are bonded to the same fluorene group may be identical or different from each other; $Ar_9$ and $Ar_{10}$ represent a substituted or unsubstituted divalent aromatic group or a substituted or unsubstituted divalent heterocyclic group, which may be identical or different from each other; $Ar_{11}$, $Ar_{12}$, $Ar_{13}$, and $Ar_{14}$ represent a substituted or unsubstituted aromatic group, a substituted or unsubstituted heterocyclic group, a substituted or unsubstituted condensed polycyclic aromatic group, or a substituted or unsubstituted condensed polycyclic heterocyclic group, which may be identical or different from each other, and $Ar_{11}$ and $Ar_{12}$ as well as $Ar_{13}$ and $Ar_{14}$ may be bonded with each other to form rings, respectively; and m represents an integral number of 1 to 10.)

Specific examples of substituents in the general formula [X] and [XI] are the same as those as in the cases of the above general formula [I] to [IX]. Typical examples of the fluorene compounds represented by the general formula [X] or [XI] will be given thereinafter, but the present invention is not limited thereto.

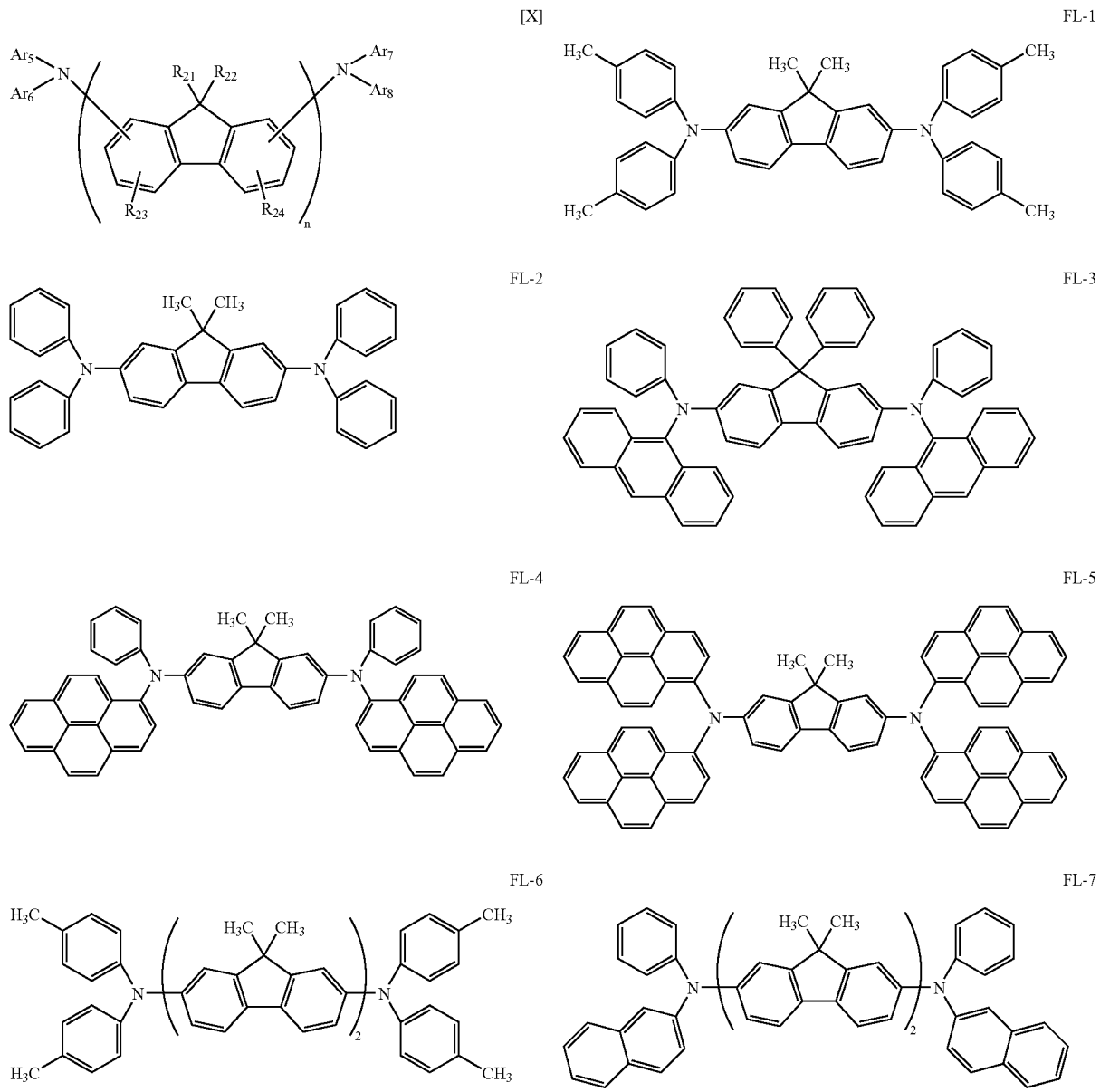

-continued
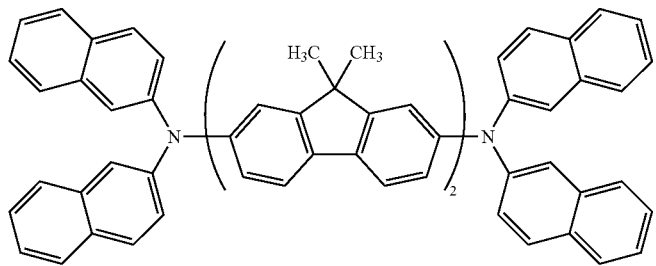
FL-8
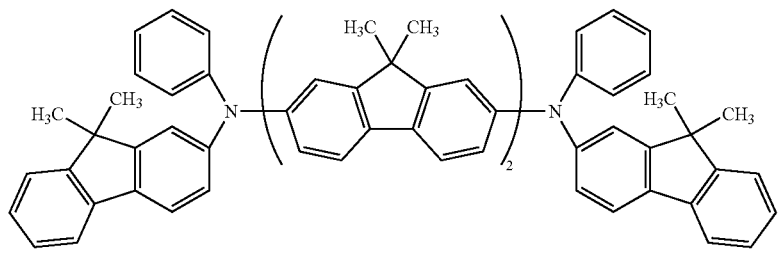
FL-9
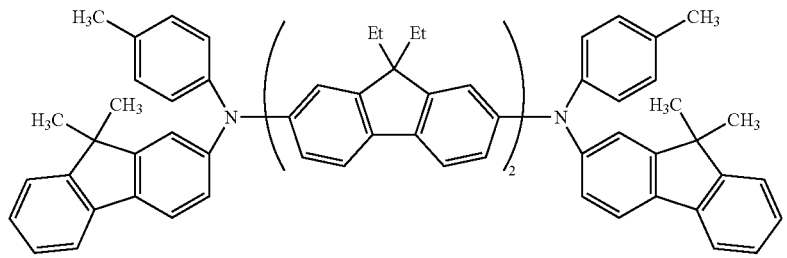
FL-10
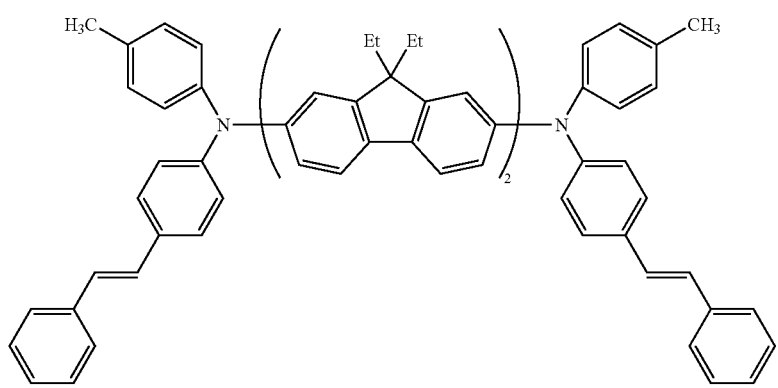
FL-11
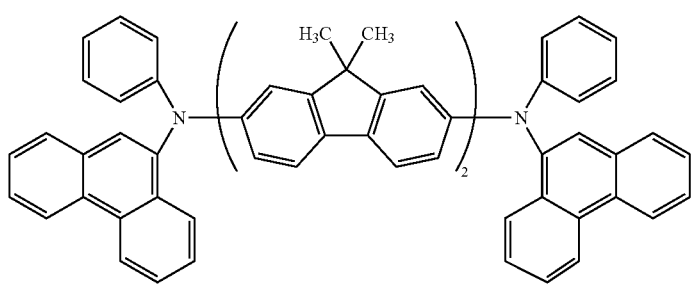
FL-12

FL-13
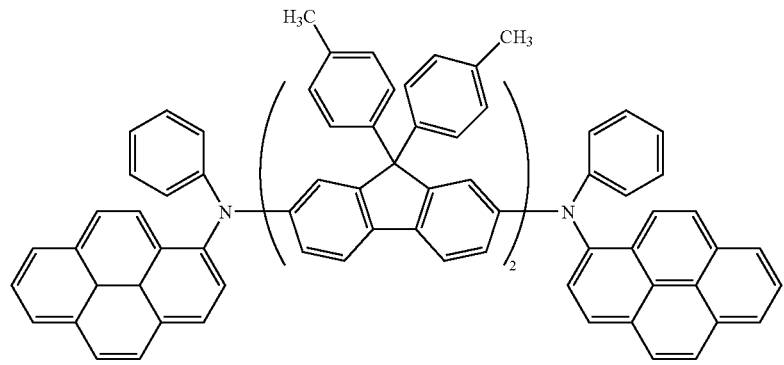
FL-14
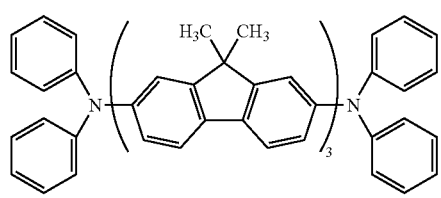
FL-15
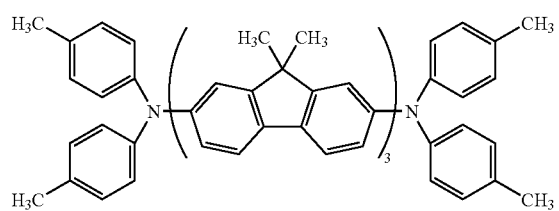
FL-16
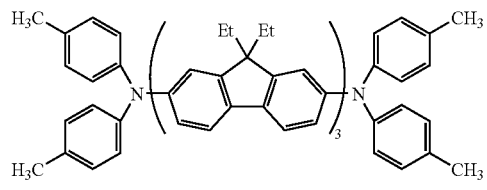
FL-17
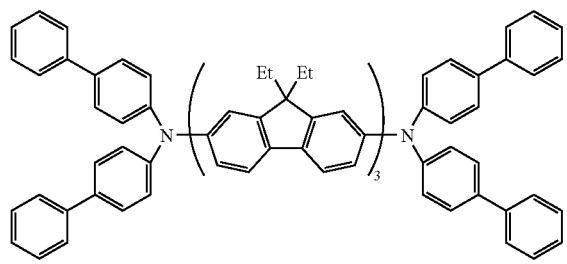
FL-18
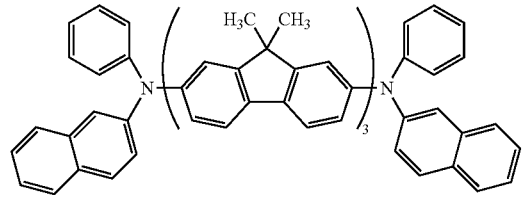
FL-19
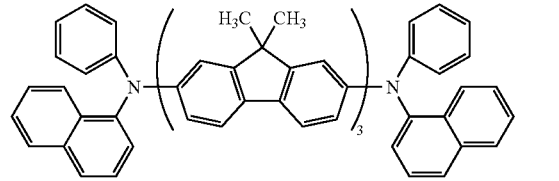
FL-20
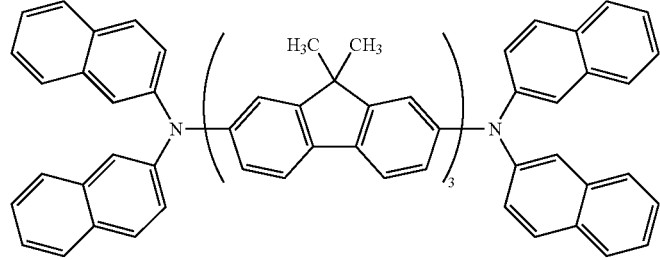
FL-21
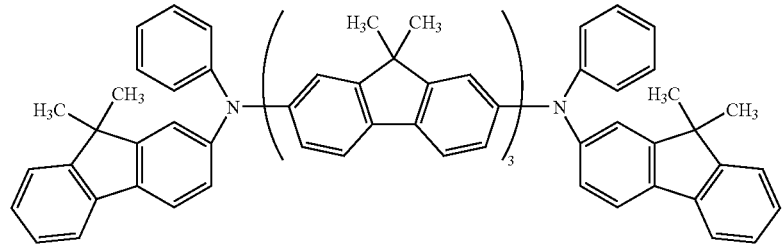

-continued
FL-22
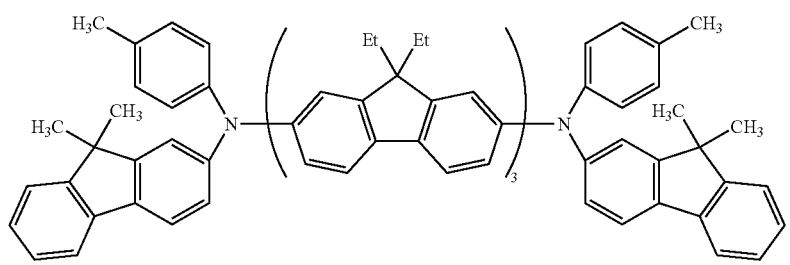
FL-23
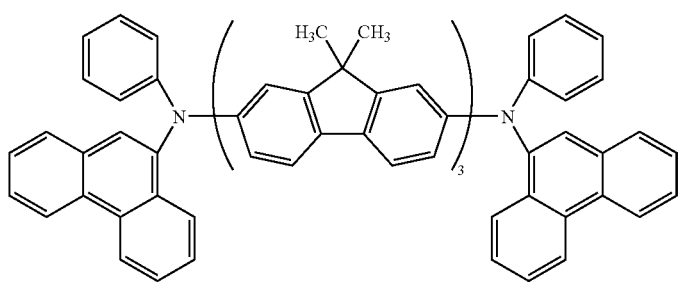
FL-24
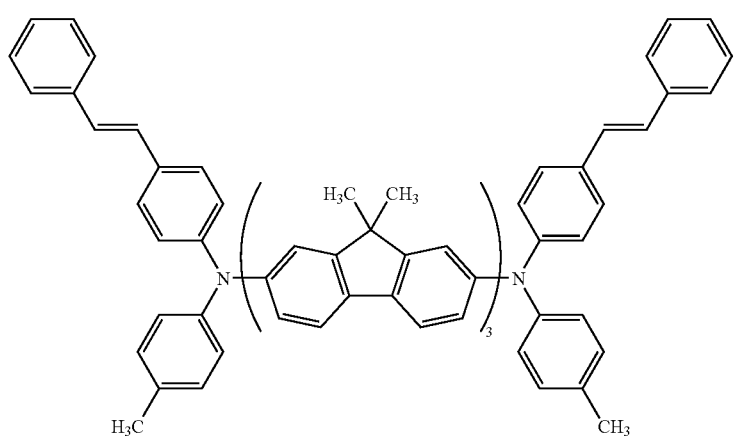
FL-25
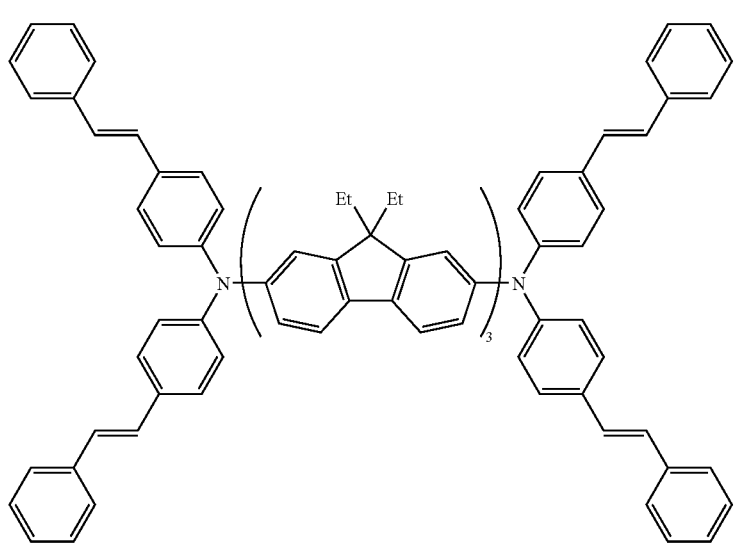

-continued
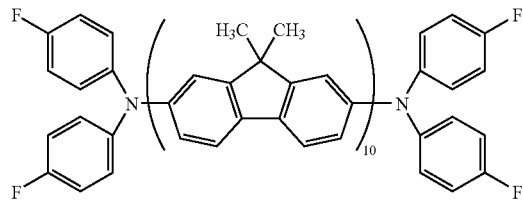
FL-26
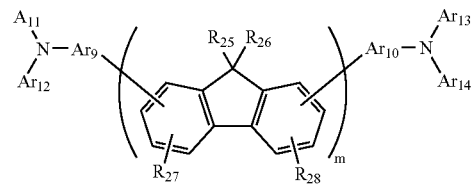
[XI]
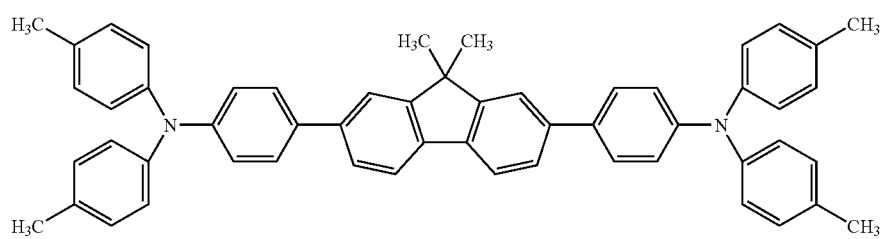
FL-27
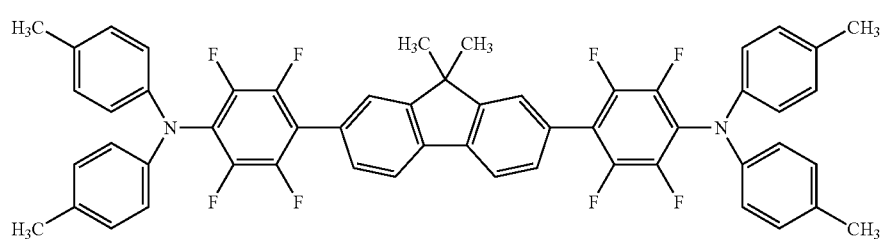
FL-28
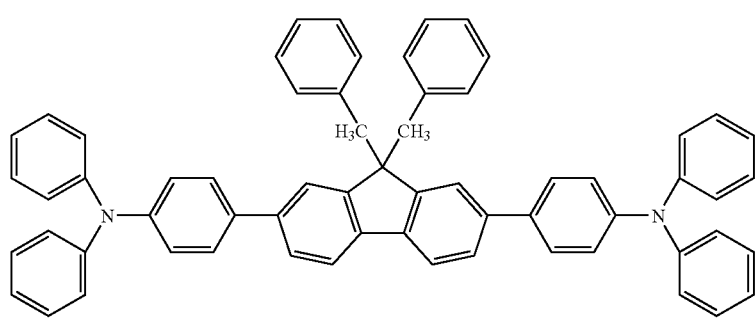
FL-29
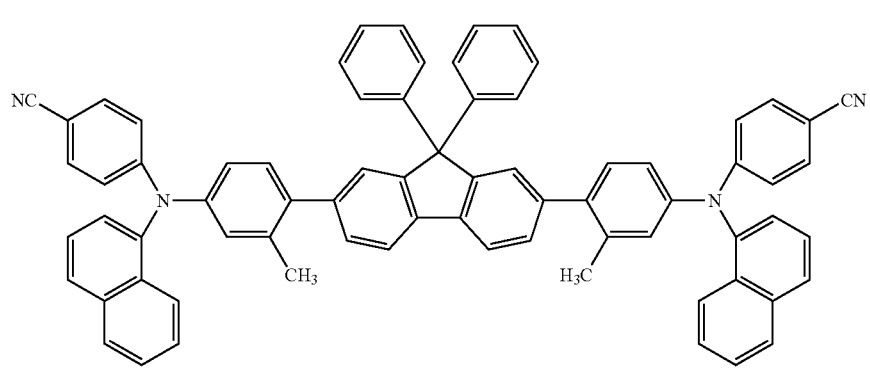
FL-30
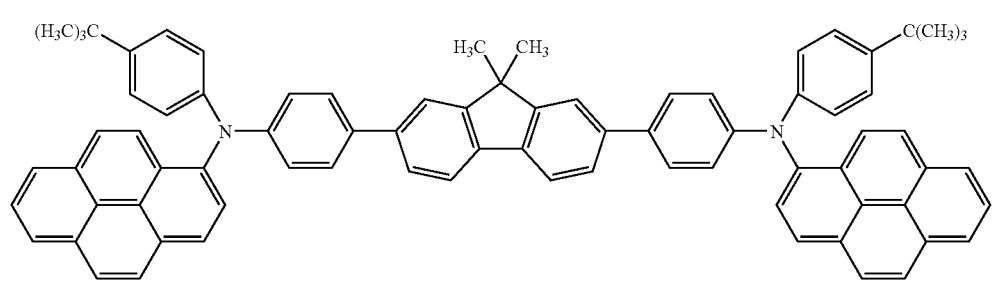
FL-31

-continued
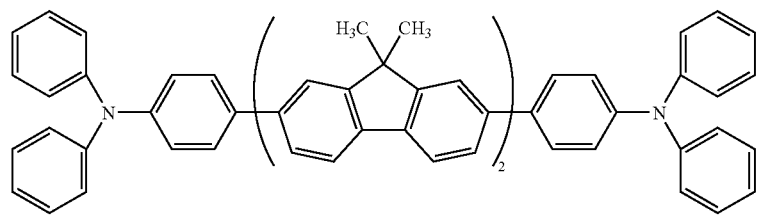
FL-32
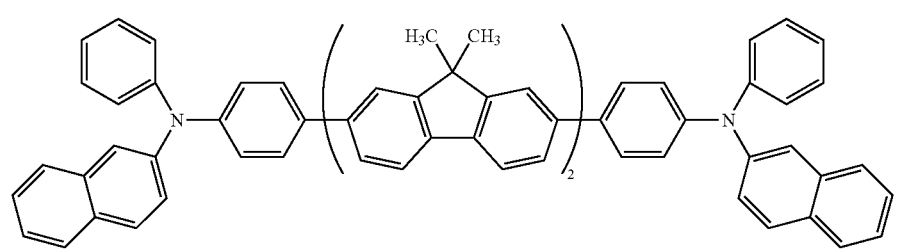
FL-33
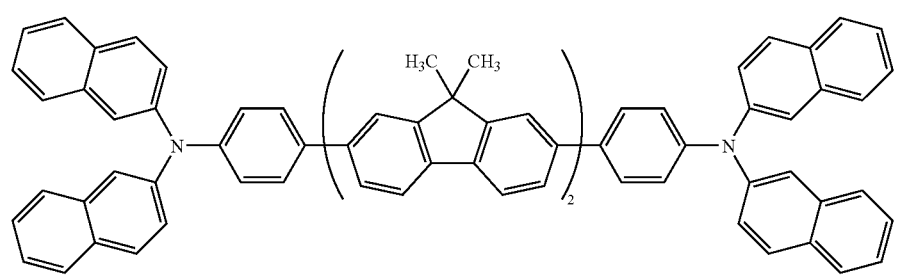
FL-34
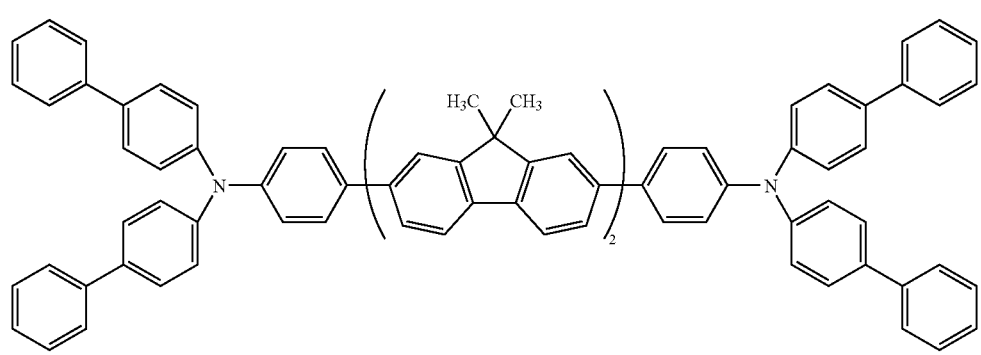
FL-35
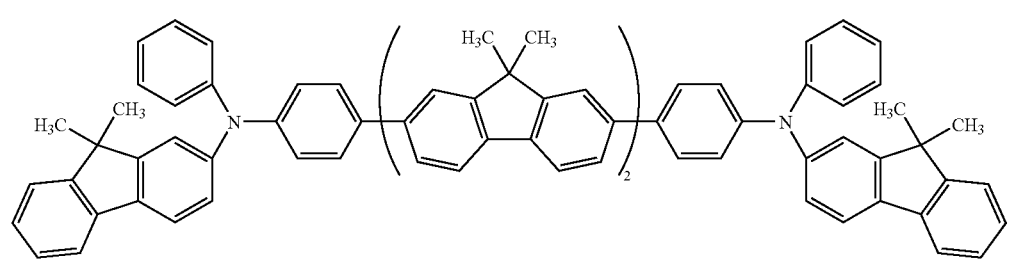
FL-36

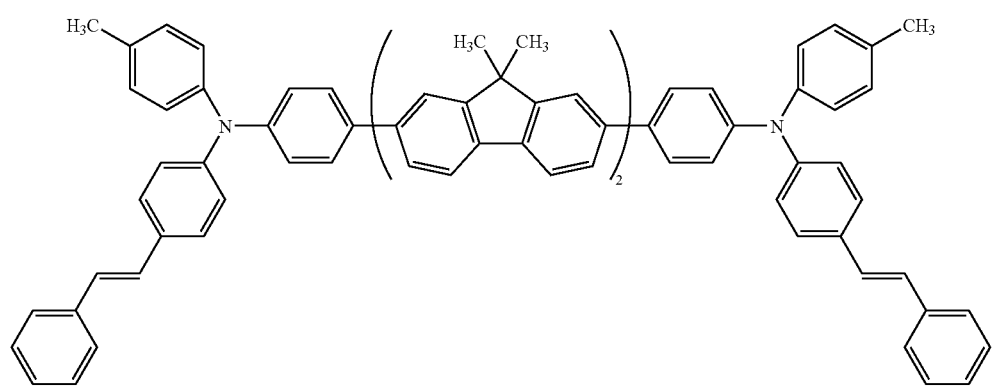
FL-37
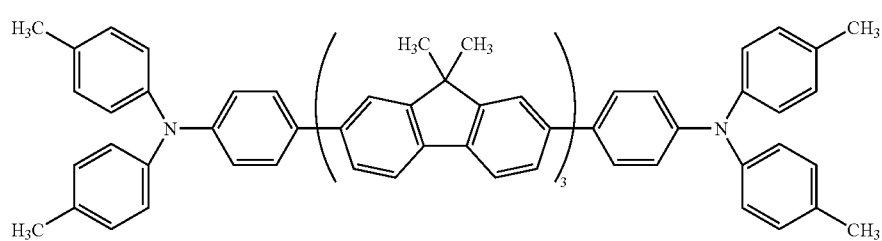
FL-38
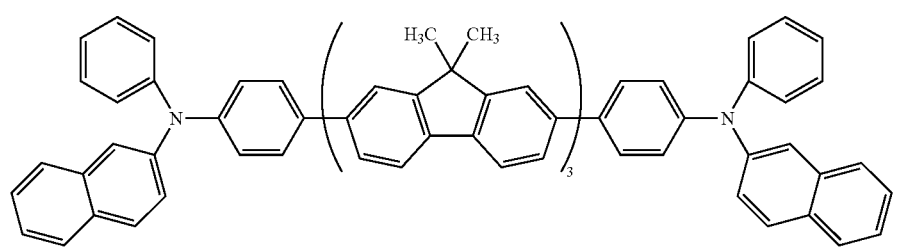
FL-39
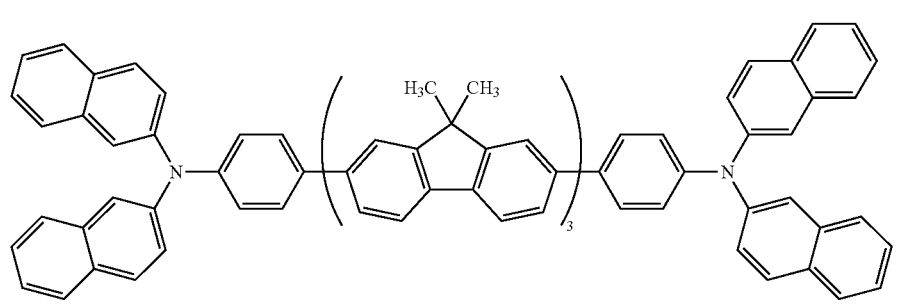
FL-40
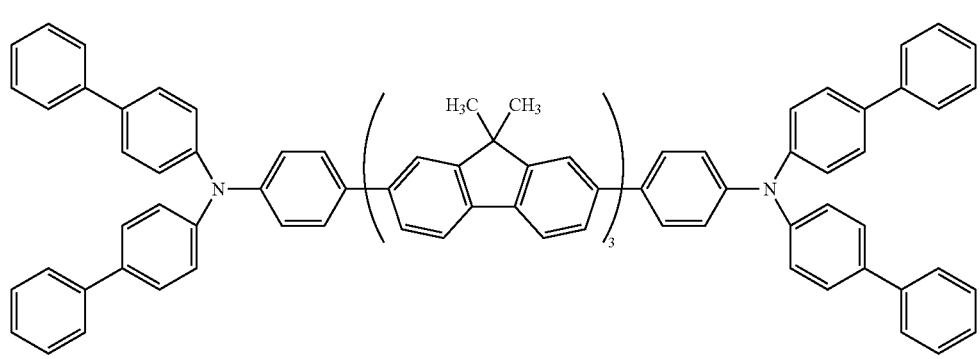
FL-41

-continued

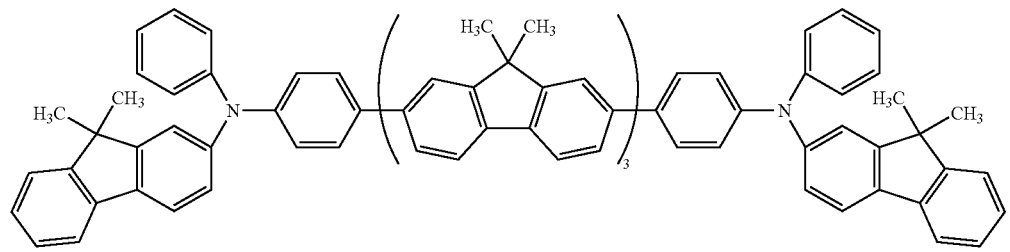
FL-42

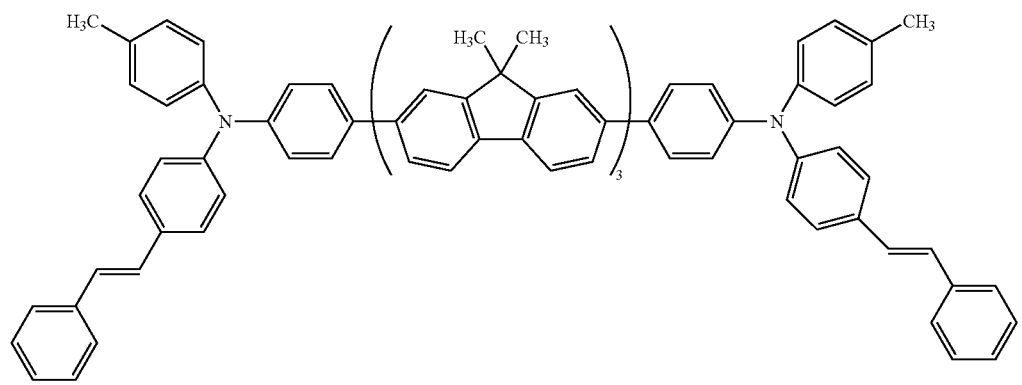
FL-43

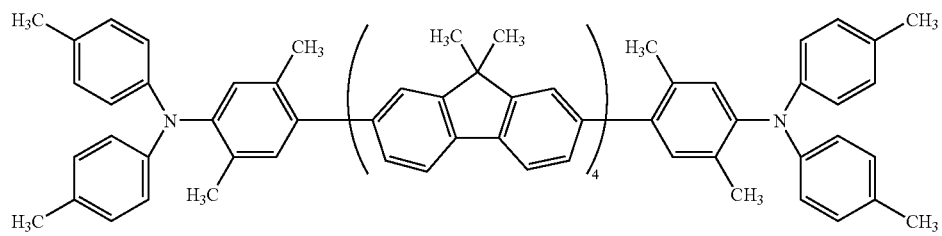
FL-44

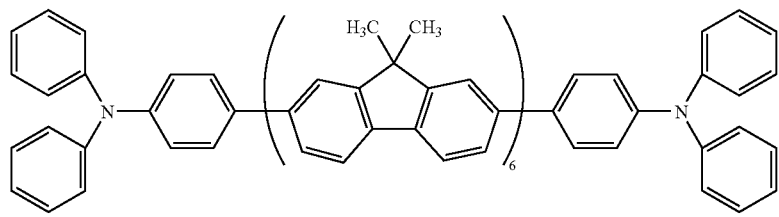
FL-45

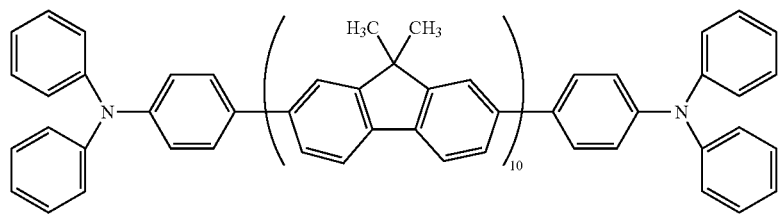
FL-46

Preferable examples of the organic luminescence device are shown in FIGS. 1 to 6, respectively.

FIG. 1 is a cross-sectional diagram that illustrates an example of the organic luminescence device of the present invention. In FIG. 1, the device comprises an anode 2, a luminescent layer 3, and a cathode 4, which are formed on a substrate 1 in that order. The luminescence device used herein is useful when it singly has a hole-transporting ability, an electron-transporting ability, and a luminescence property in itself or when it is used in combination with compounds having those characteristics.

Figure 2:
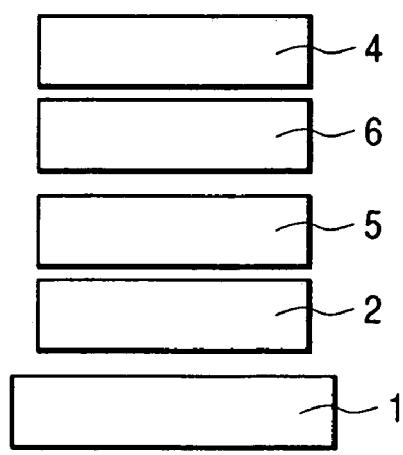
FIG. 2 is a cross-sectional diagram that illustrates another example of the organic luminescence device in accordance with the present invention.

FIG. 2 is a cross-sectional diagram that illustrates another example of the organic luminescence device of the present invention. In FIG. 2, the device comprises an anode 2, a hole-transporting layer 5, an electron-transporting layer 6, and a cathode 4, which are formed on a substrate 1 in that order. In this case, a luminescent material is useful when a material having one or both of a hole-transporting property and an electron-transporting property is used for the respective layers and is used in combination with a hole-transporting material or an electron-transporting material having no luminescence property. In addition, in this case, the luminescent layer 3 is composed of either the hole-transporting layer 5 or the electron-transporting layer 6.

Figure 3:
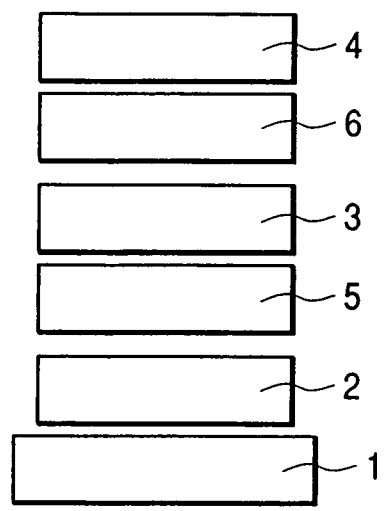
FIG. 3 is a cross-sectional diagram that illustrates another example of the organic luminescence device in accordance with the present invention.

FIG. 3 is a cross-sectional diagram that illustrates another example of the organic luminescence device of the present invention. In FIG. 3, the device comprises an anode 2, a hole-transporting layer 5, a luminescent layer 3, an electron-transporting layer 6, and a cathode 4, which are formed on a substrate 1 in that order. This is one in which a carrier-transporting function and a luminescence function are separated from each other, and is used appropriately in combination with compounds having a hole-transporting property, an electron-transporting property, and a luminescence property, respectively. Thus, the degree of freedom in selecting a material increases extremely. In addition, various kinds of compounds having different luminescent wavelengths can be used. Therefore, the diversity of luminescence hue can be allowed. Furthermore, it also becomes possible to increase the luminescence efficiency by effectively confining each carrier or exciton in the middle luminescent layer 3.

Figure 4:
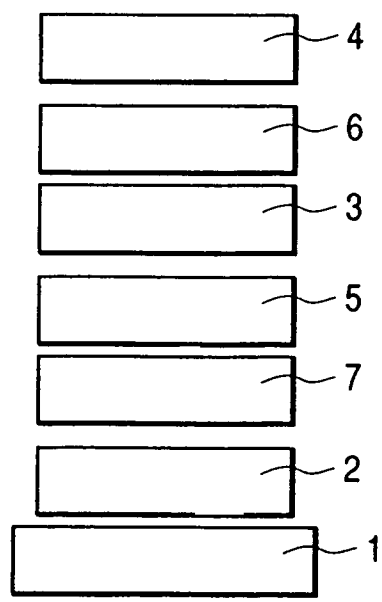
FIG. 4 is a cross-sectional diagram that illustrates another example of the organic luminescence device in accordance with the present invention.

FIG. 4 is a cross-sectional diagram that illustrates another example of the organic luminescence device of the present invention. In FIG. 4, as compared with the example of FIG. 3, the device is constructed such that a hole-injection layer 7 is inserted in the anode 2 side. It is effective in the improvement of an adhesion between the anode 2 and the hole-transporting layer 5 or the improvement of an injection property of holes, so that it is effective in lowering voltage.

Figure 5:
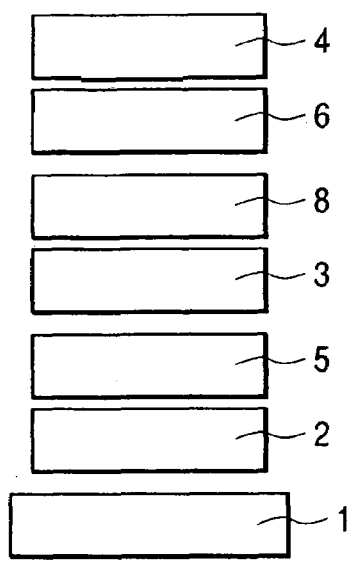
FIG. 5 is a cross-sectional diagram that illustrates another example of the organic luminescence device in accordance with the present invention.
Figure 6:
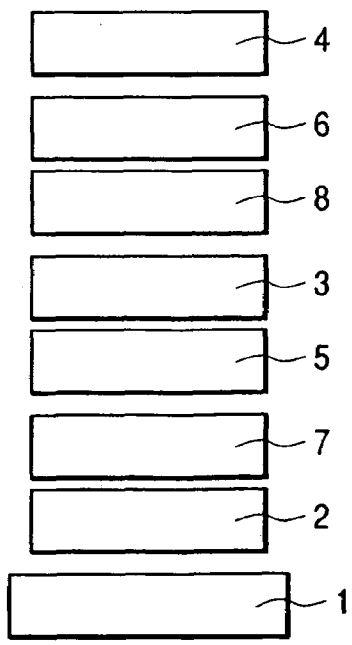
FIG. 6 is a cross-sectional diagram that illustrates another example of the organic luminescence device in accordance with the present invention.

FIGS. 5 and 6 are cross-sectional diagrams that illustrate other examples of the organic luminescence device of the present invention, respectively. In FIGS. 5 and 6, as compared with the examples of FIGS. 3 and 4, the device is constructed such that a layer (a hole-blocking layer 8) that prevents a hole or an exciton from passing toward the cathode 4 side is inserted between the luminescent layer 3 and the electron-transporting layer 6. The use of a compound having an extremely high ionization-potential as the hole-blocking layer 8 allows a configuration effective to an improvement in luminescence efficiency.

However, in FIGS. 1 to 6, there are shown common basic device configurations. The configuration of the organic luminescence device using the compound of the present invention is not limited thereto. For instance, it is possible to adopt various layer configurations such as one in which an insulating layer is formed at the interface between the electrode and the organic layer, one in which an adhesive layer or an interference layer is formed, and one in which the hole-transporting layer is composed of two layers with different ionization potentials.

The spiro compounds represented by the general formula [I] or the general formula [II] to be used in the present invention are compounds each having excellent electron-transporting property, luminescence property, and durability as compared with the conventional compounds, and-they can be used in any modes of FIGS. 1 to 6.

In the present invention, the spiro compounds represented by the general formula [I] or the general formula [II] are used as structural components of the electron-transporting layer or the luminescent layer. However, hole-transporting compounds, luminescent compounds, electron-transporting compounds, or the like, which have been known, may be used together if required.

The examples of those compounds will be given below.

Hole-transporting Compound

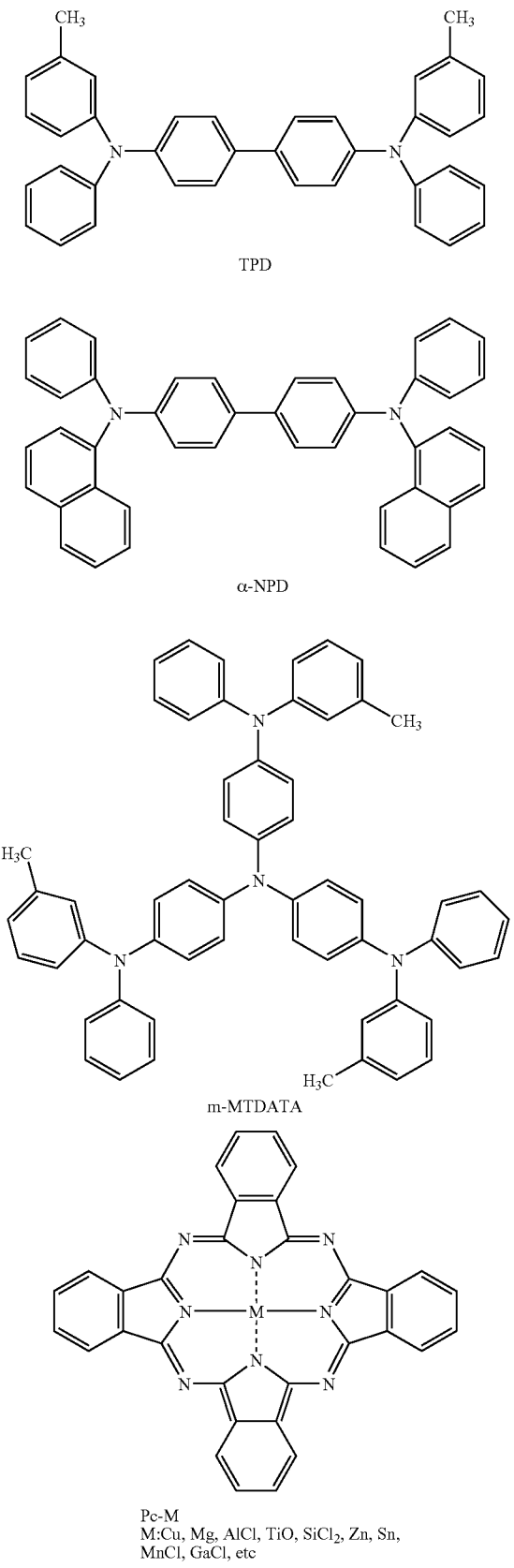

TPD

α-NPD m-MTDATA

Pc-M
M:Cu, Mg, AlCl, TiO, SiCl$_2$, Zn, Sn, MnCl, GaCl, etc

-continued
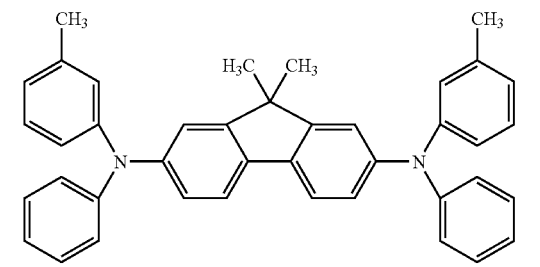
DTDPFL
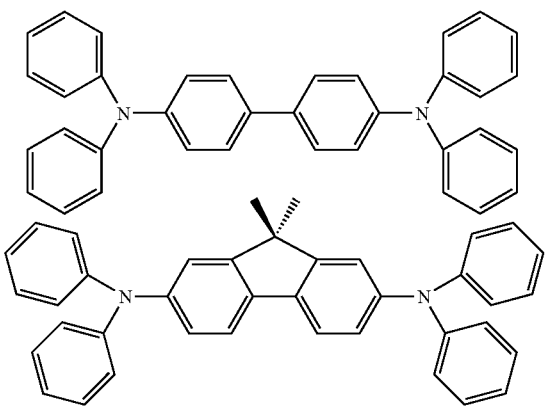
spiro-TPD
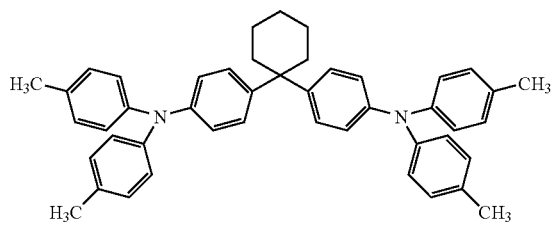
TPAC
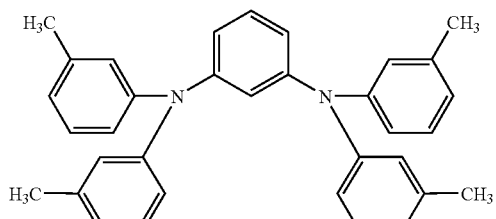
PDA
Electron-transporting Luminescent Material
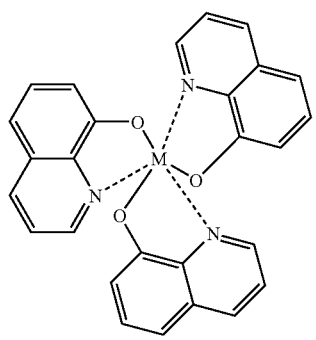
M: Al, Ga
-continued
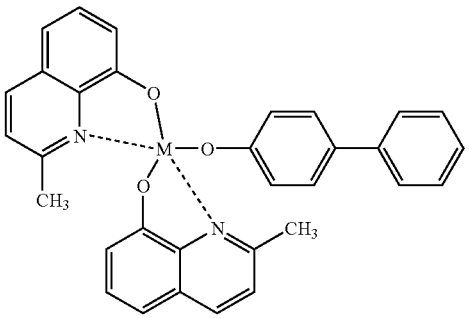
M: Al, Ga
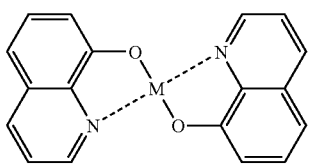
M: Zn, Mg, Be
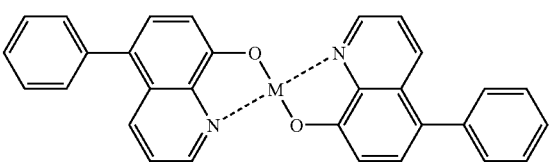
M: Zn, Mg, Be
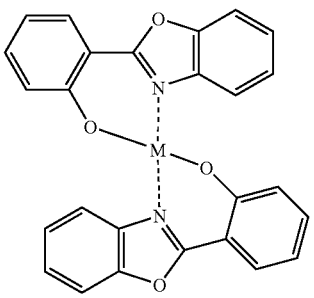
M: Zn, Mg, Be
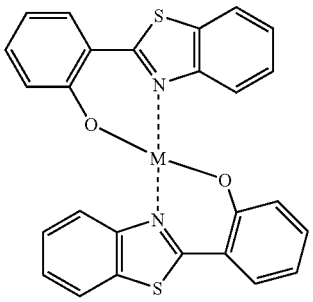
M: Zn, Mg, Be

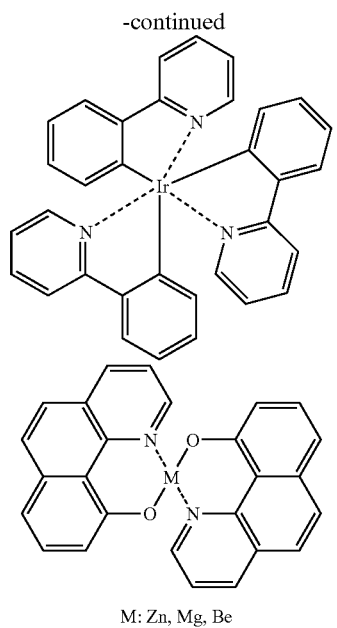
M: Zn, Mg, Be
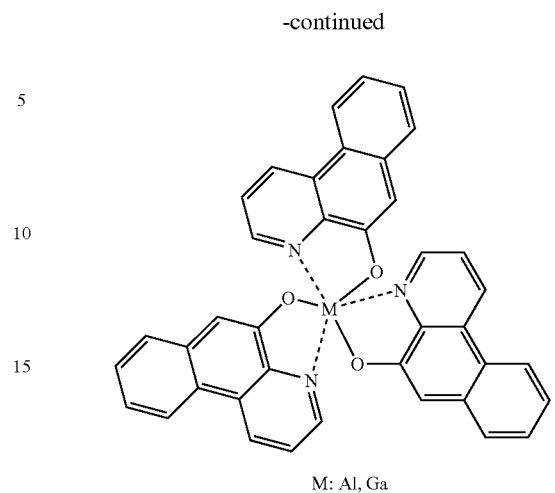
M: Al, Ga
Luminescent Material
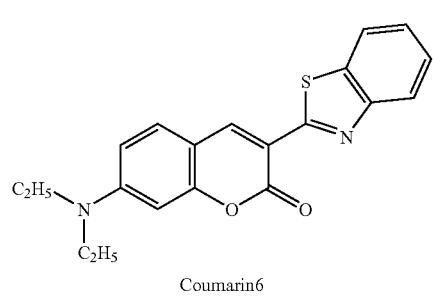
Coumarin6
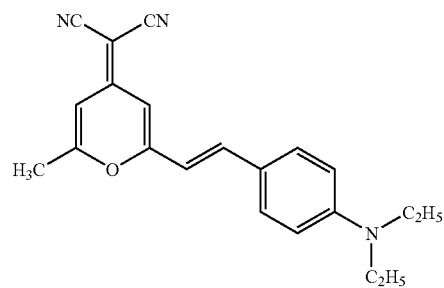
DCM-1
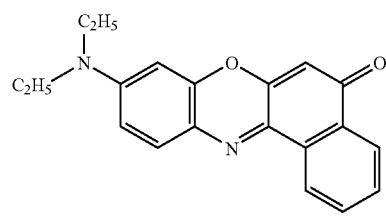
Nile red
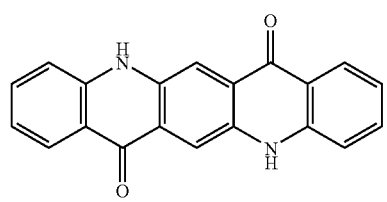
Quinacridone
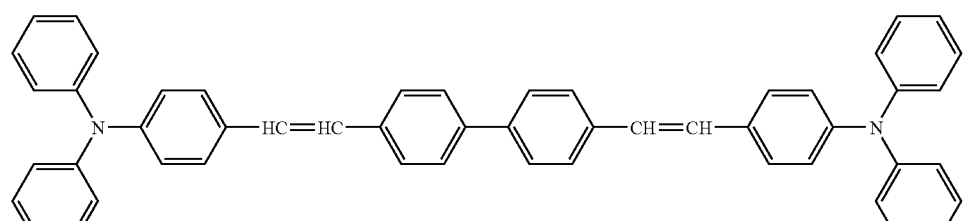
DTPABVi

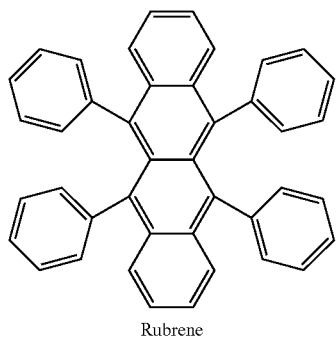
Rubrene
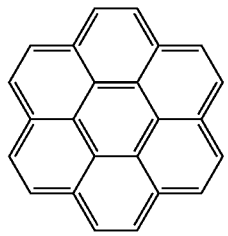
Coronene
Luminescent Layer Matrix Material and Electron-transporting Material
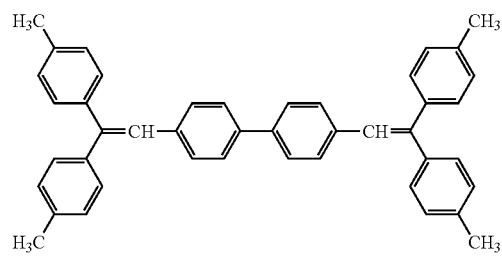
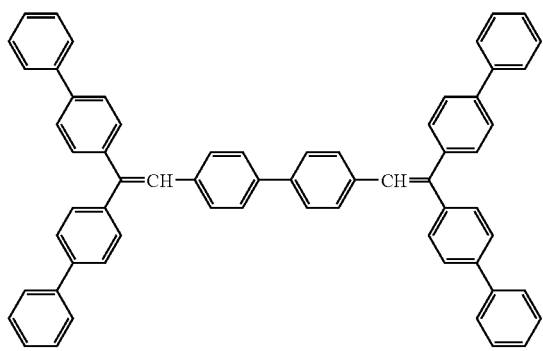
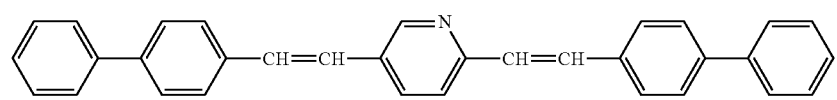
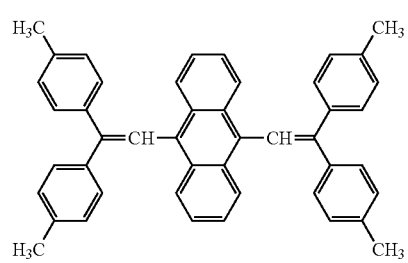
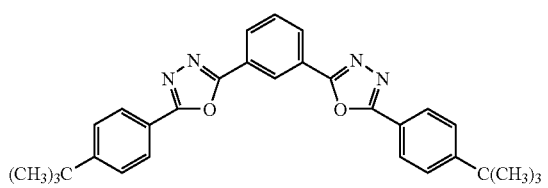
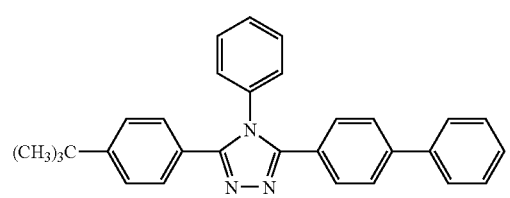
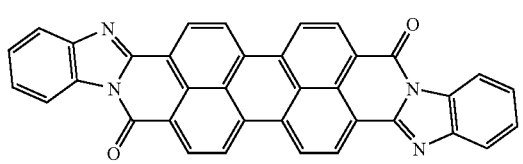
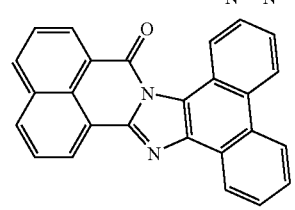
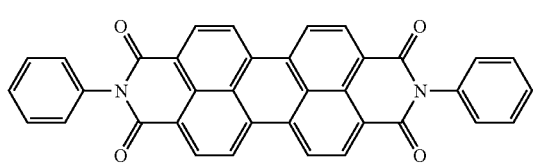

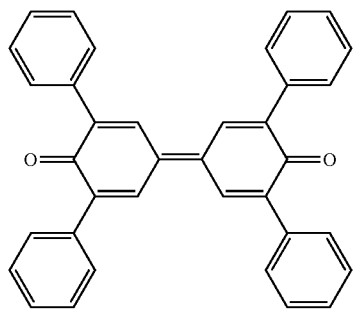
-continued
Polymeric Hole-transporting Material
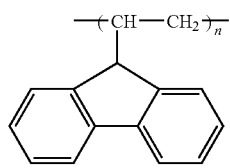
PVCz
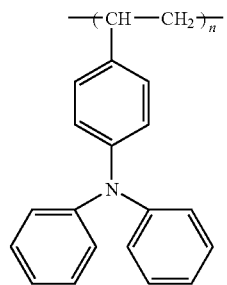
DPA-PS
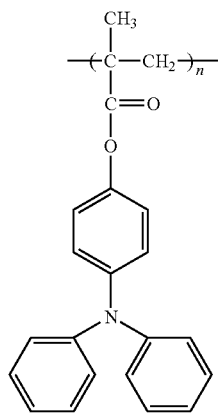
TPA-PMMA
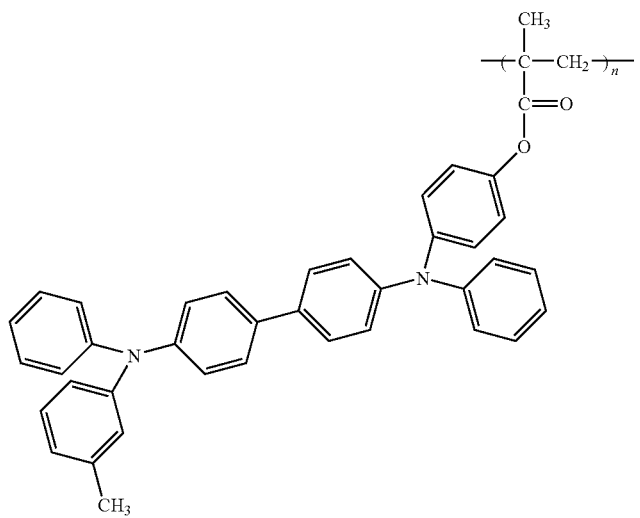
TPD-PMMA

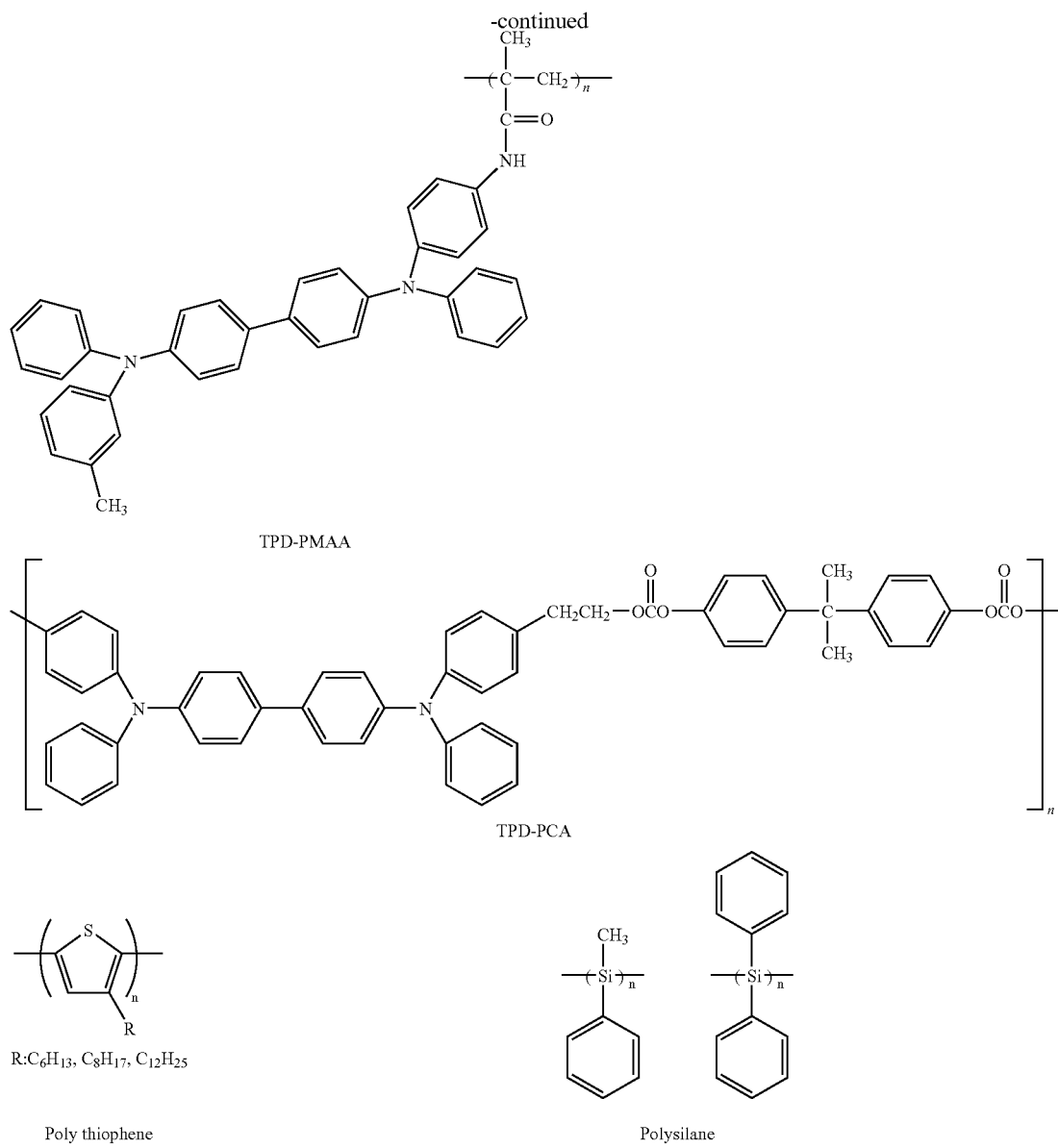
TPD-PMAA
TPD-PCA
Poly thiophene
R: $C_6H_{13}$, $C_8H_{17}$, $C_{12}H_{25}$
Polysilane
Polymeric Luminescent Material and Charge-transporting Material
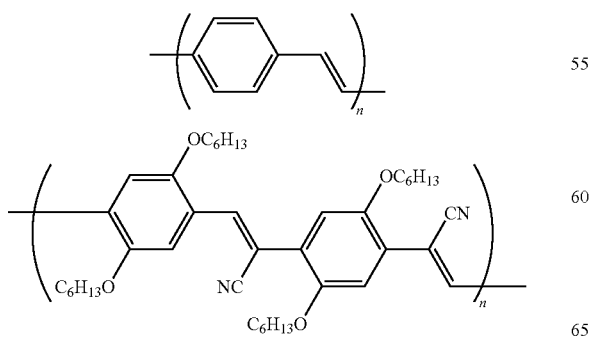
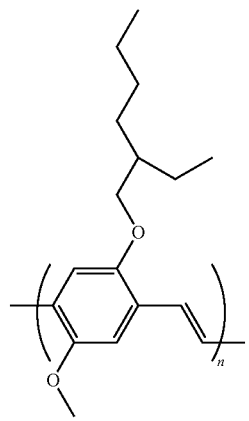

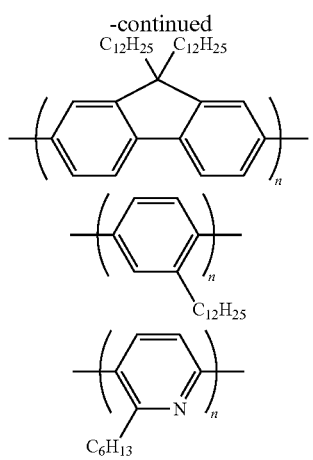

In the organic luminescence device of the present invention, the layer containing the spiro compound represented by the general formula [I] or the general formula [II] and the layer containing another organic compound are generally formed as thin films by a vacuum evaporation method, or by a coating method after being dissolved in an appropriate solvent. In particular, in the case of forming a film with a coating method, the film may be formed in combination with an appropriate binder resin.

The above binder resin can be selected from a wide variety of the binder resins including, for example, polyvinyl carbazole resin, polycarbonate resin, polyester resin, polyarylate resin, polystyrene resin, acrylic resin, methacryl resin, butyral resin, polyvinyl acetal resin, diallyl phthalate resin, phenol resin, epoxy resin, silicone resin, polysulfone resin, and urea resin, although not limited to them. In addition, those resins may be used solely or one or more resins may be combined with each other as a copolymer.

The anode material may be one preferably having a large work function. For example, a simple metal substance such as gold, platinum, nickel, palladium, cobalt, selenium, or vanadium, or an alloy thereof, or a metal oxide such as tin oxide, zinc oxide, indium tin oxide (ITO), or indium zinc oxide can be used. In addition, a conductive polymer such as polyaniline, polypyrrole, polythiophene, or polyphenylene sulfide can be also used. Those electrode substances may be used solely or two or more substances may be used together.

On the other hand, the cathode material may be one preferably having a small work function. For example, a simple metal substance such as lithium, sodium, potassium, cesium, calcium, magnesium, aluminum, indium, silver, lead, tin, or chromium, or an alloy of plural substances can be used. It is also possible to use a metal oxide such as indium tin oxide (ITO). In addition, the cathode may be constructed as a single layer or may have a multi-layer configuration.

The substance used in the present invention may be, although not particularly limited to, a non-transparent substrate such as a metallic substrate or a ceramic substrate, or a transparent substrate formed of glass, quartz, plastic sheets, or the like. In addition, it is also possible to control the luminescence color light by using a color filter film, a fluorescent color-converting filter film, or a dielectric reflection film as a substrate.

Furthermore, a protective layer or a sealing layer may be formed on the prepared device for preventing the device from contacting with oxygen, moisture, or the like. The protective layer may be a diamond thin film, a film made of an inorganic material such as a metal oxide or a metal nitride, or a polymer film made of a fluorocarbon resin, polyparaxylene, polyethylene, a silicone resin, or a polystyrene resin, or furthermore it may be a photo-curing resin. Furthermore, it is also possible to package the device itself with an appropriate sealing resin while covering it with a glass, a gas-impermeable film, a metal, or the like.

EXAMPLES

Hereinafter, the present invention will be described more specifically with examples. However, the present invention is not limited to those examples.

Synthesis Example 1

[Synthesis of Exemplified Compound No. 1]

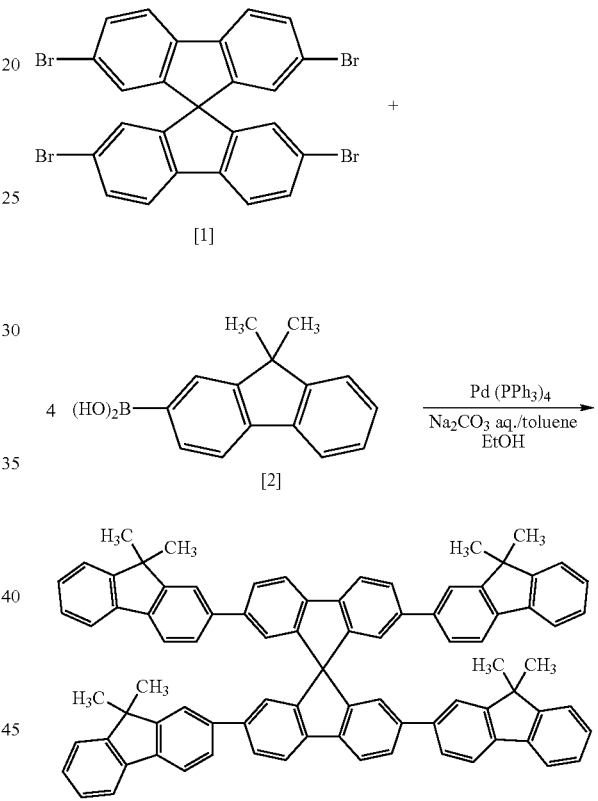

*1) *J. Org. chem.*, 61, 6906-6921, 1996.

In a 500-ml three-neck flask, 2.0 g (3.16 mmol) of 2,2'-7,7'-tetrabromo-9,9'-spirobifluorene [1]*1), 4.5 g (19.0 mmol) of 9,9-dimethylfluorene-2-boronic acid [2], 140 ml of toluene, and 70 ml of ethanol were added, and an aqueous solution of 25 g of sodium carbonate/130 ml of water was dropped thereto with stirring in a nitrogen atmosphere at room temperature, followed by the addition of 0.7 g (0.63 mmol) of tetrakis (triphenylphosphine) palladium (0). After stirring the mixture for 30 minutes at room temperature, the temperature is allowed to rise to 77° C., followed by stirring for 8 hours. After the reaction, an organic layer was extracted with chloroform and was then dried with anhydrous sodium sulfate, followed by purification with a silica gel column (hexane+toluene mixture developing solvent). Consequently, 2.5 g (73% yield) of the exemplified compound No. 1 (white crystal) was obtained.

Synthesis Example 2

[Synthesis of Exemplified Compound No. 7]

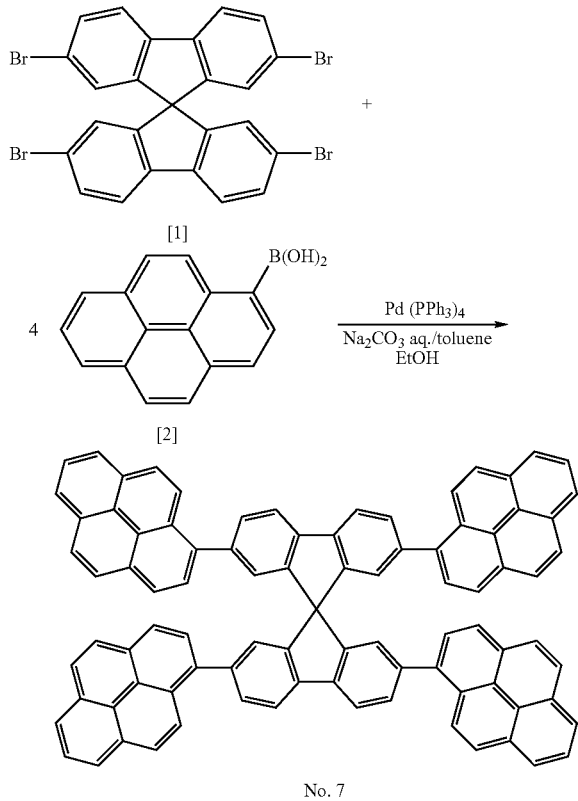

In a 500-ml three-neck flask, 2.0 g (3.16 mmol) of 2,2'-7,7'-tetrabromo-9,9'-spirobifluorene [1], 4.7 g (19.0 mmol) of pyrene-1-boronic acid [2], 140 ml of toluene, and 70 ml of ethanol were added, and an aqueous solution of 25 g of sodium carbonate/130 ml of water was dropped with stirring in a nitrogen atmosphere at room temperature, followed by the addition of 0.7 g (0.63 mmol) of tetrakis (triphenylphosphine) palladium (0). After stirring the mixture for 30 minutes at room temperature, the temperature is allowed to rise to 77° C., followed by stirring for 8 hours. After the reaction, an organic layer was extracted with chloroform and was then dried with anhydrous sodium sulfate, followed by purification with a silica gel column (hexane+toluene mixture developing solvent). Consequently, 2.3 g (65% yield) of the exemplified compound No. 7 (white crystal) was obtained.

Synthesis Example 3

[Synthesis of Exemplified Compound No. 14]

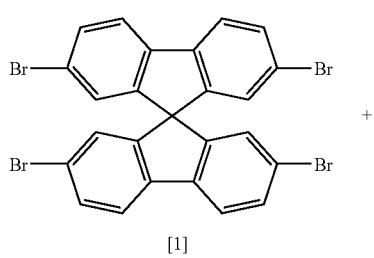

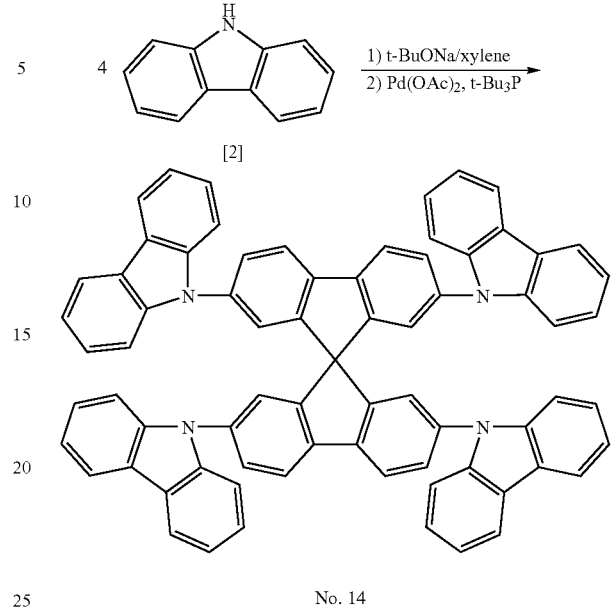

In a 300-ml three-neck flask, 2.0 g (3.16 mmol) of 2,2'-7,7'-tetrabromo-9,9'-spirobifluorene [1], 3.2 g (19.0 mmol) of carbazole [2], and 150 ml of xylene were added, and 2.0 g (20.9 mmol) of t-butoxy sodium was added thereto with stirring in a nitrogen atmosphere at room temperature, followed by heating the mixture to a temperature of 50° C. In this mixture, a 5-ml xylene solution of 0.035 g (0.16 mmol) of palladium acetate and 0.032 g (0.16 mmol) of tri-t-butylphosphine was added, followed by heating the mixture to 130° C. and stirring for 8 hours. After the reaction, an organic layer was extracted with chloroform and was then dried with anhydrous sodium sulfate, followed by purification with a silica gel column (hexane+toluene mixture developing solvent). Consequently, 1.7 g (55% yield) of the exemplified compound No. 14 (white crystal) was obtained.

Synthesis Example 4

[Synthesis of Exemplified Compound No. 20]

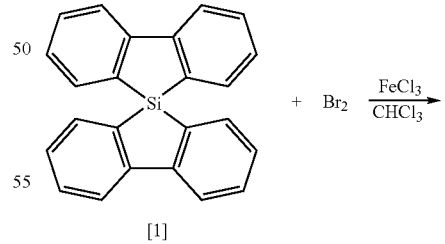

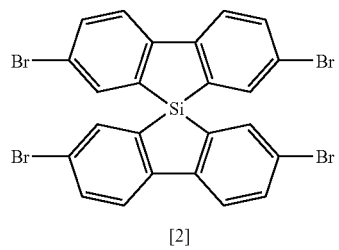

-continued

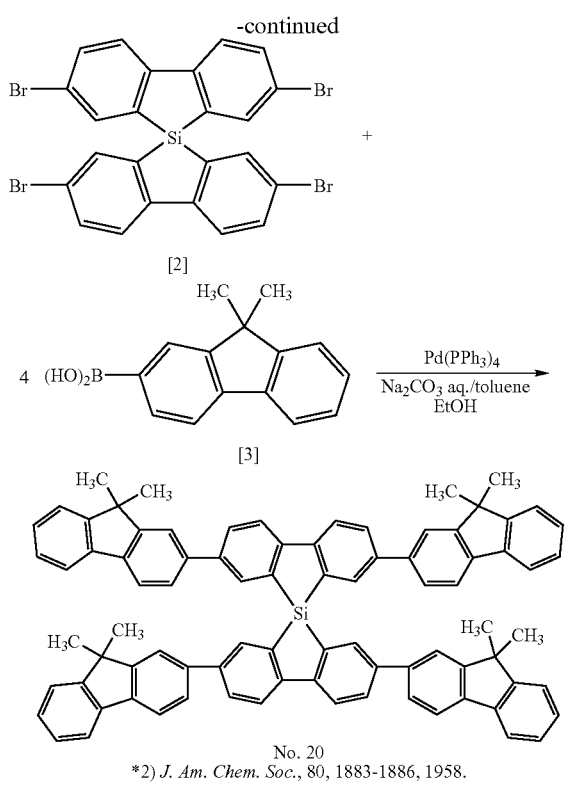

No. 20
*2) *J. Am. Chem. Soc.*, 80, 1883-1886, 1958.

In a 300-ml three-neck flask, 3.0 g (9.02 mmol) of 5,5'-spirobi(dibenzosilole) [1]*2) and 100 ml of chloroform were added, and then 0.07 g (0.45 mmol) of iron chloride (III) was added with stirring at 0° C., followed by dropping 5.9 g (37.0 mmol) of bromine. After stirring the mixture for 6 hours at room temperature, an organic layer was extracted with chloroform and was then washed with a sodium thiosulfate aqueous solution, followed by drying with anhydrous sodium sulfate. A crystal obtained by distilling off the solvent was re-crystallized with chloroform, resulting in 4.0 g (69% yield) of tetrabromo-5,5'-spiro(dibenzosilole) [2] (white crystal).

Next, in a 500-ml three-neck flask, 2.0 g (3.09 mmol) of [2], 4.4 g (18.5 mmol) of 9,9-dimethylfluorene-2-boronic acid [3], 140 ml of toluene, and 70 ml of ethanol were added, and an aqueous solution of 25 g of sodium carbonate/130 ml of water was dropped in a nitrogen atmosphere, followed by the addition of 0.5 g (0.43 mmol) of tetrakis (triphenylphosphine) palladium (0). After stirring the mixture for 30 minutes at room temperature, the temperature is allowed to rise to 77° C., followed by stirring for 8 hours. After the reaction, an organic layer was extracted with chloroform and was then dried with anhydrous sodium sulfate, followed by purification with a silica gel column (hexane+toluene mixture developing solvent). Consequently, 2.2 g (64% yield) of the exemplified compound No. 20 (white crystal) was obtained.

Example 1

A device having the structure shown in FIG. 2 was prepared.

On a glass substrate as a substrate 1, indium tin oxide (ITO) is deposited into a film with a thickness of 120 nm by a sputtering method to obtain an anode 2, so that the substrate thus formed is used as a transparent conductive support substrate. This was sequentially subjected to ultrasonic cleanings with acetone and isopropyl alcohol (IPA), and was then washed with IPA by boiling, followed by drying. Furthermore, one subjected to UV/ozone cleaning was used as a transparent conductive support substrate.

On the transparent conductive support substrate, a chloroform solution of the compound represented by the following structural formula was coated into a film of 30 nm in thickness by a spin-coating method, resulting in a hole-transporting layer 5.

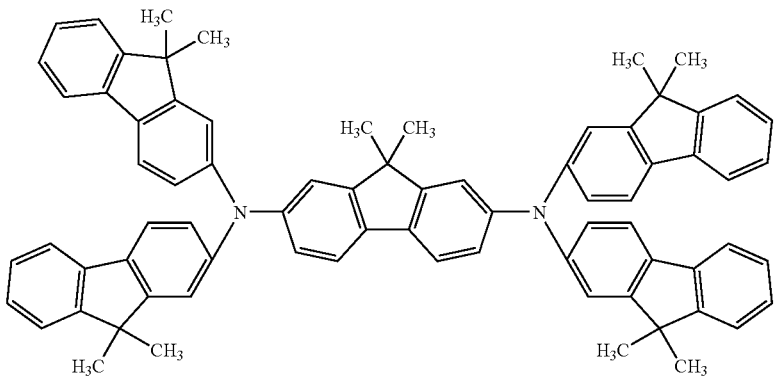

Furthermore, an electron-transporting layer 6 was formed by forming a film of 50 nm in thickness from a spiro compound represented by the exemplified compound No. 1 by a vacuum evaporation method. The film formation was performed under the conditions in which the degree of vacuum at the time of evaporation was $1.0 \times 10^{-4}$ Pa and the film formation rate was 0.2 to 0.3 nm/sec.

A metal layer film of 50 nm in thickness was formed on the above organic layer as a cathode 4 by using an evaporation material including aluminum and lithium (lithium concentration: 1% by atom) by a vacuum evaporation method, and further an aluminum layer of 150 nm in thickness was formed by a vacuum evaporation method. The film formation was performed under the conditions in which the degree of vacuum at the time of evaporation was $1.0 \times 10^{-4}$ Pa and the film formation rate was 1.0 to 1.2 nm/sec.

Furthermore, the resulting product was covered with a protective glass plate in a nitrogen atmosphere and was then sealed with an acrylic resin adhesive.

When a direct current voltage of 10 V was applied on the device obtained in this way with an ITO electrode (anode 2) provided as a positive electrode and an Al—Li electrode (cathode 4) provided as a negative electrode, the current was caused to flow into the device at a current density of 11.5 mA/cm$^2$ and blue-colored luminescence at a luminance of 3800 cd/m$^2$ was observed.

Furthermore, when the current density was kept at 10.0 mA/cm$^2$ and the voltage was applied for 100 hours, an initial luminance of 3500 cd/m$^2$ changed to a luminance of 3300 cd/m$^2$ after 100 hours, indicating small deterioration of luminance.

Examples 2 to 10

Devices were prepared and evaluated in the same way as that of Example 1, except that the exemplified compounds shown in Table 1 were used in place of the exemplified compound No. 1. The results are shown in Table 1.

Comparative Examples 1 to 3

Devices were prepared and evaluated in the same way as that of Example 1, except that the compounds represented by the following structural formula were used in place of the exemplified compound No. 1. The results are shown in Table 1.

Comparative Compound No. 1

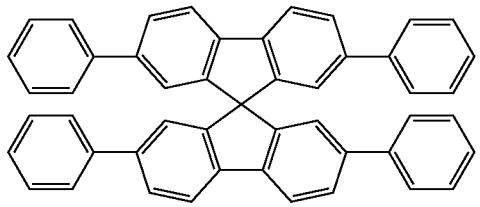

Comparative Compound No. 2

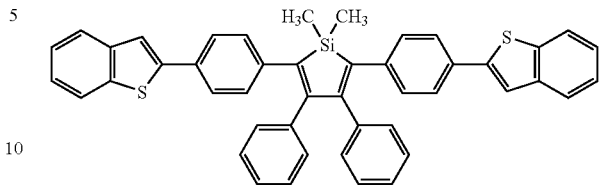

Comparative Compound No. 3

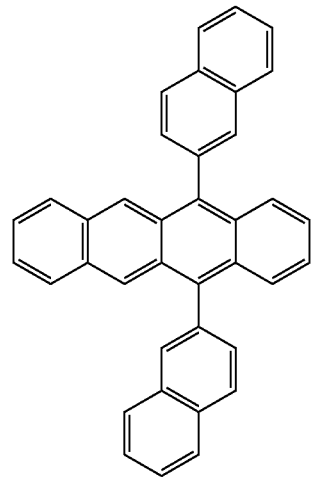

TABLE 1

| | | Initial stage | | Durability | | |
| --- | --- | --- | --- | --- | --- | --- |
| Example No. | Exemplified compound No. | Applied voltage (V) | Luminance (cd/m$^2$) | Current density (mA/cm$^2$) | Initial luminance (cd/m$^2$) | Luminance after 100-hour (cd/m$^2$) |
| Example 1 | 1 | 10 | 3800 | 10.0 | 3500 | 3300 |
| 2 | 5 | 10 | 4500 | 10.0 | 4100 | 3800 |
| 3 | 7 | 10 | 3500 | 10.0 | 3300 | 3200 |
| 4 | 10 | 10 | 2900 | 10.0 | 2700 | 2500 |
| 5 | 13 | 10 | 3800 | 10.0 | 3500 | 3400 |
| 6 | 16 | 10 | 2400 | 10.0 | 2200 | 1900 |
| 7 | 18 | 10 | 2400 | 10.0 | 2300 | 2200 |
| 8 | 21 | 10 | 3600 | 10.0 | 3500 | 3300 |
| 9 | 24 | 10 | 2700 | 10.0 | 2600 | 2200 |
| 10 | 27 | 10 | 2300 | 10.0 | 2100 | 2000 |
| Comparative Example 1 | Comparative 1 | 10 | 850 | 10.0 | 800 | 550 |
| 2 | Comparative 2 | 10 | 700 | 10.0 | 650 | 250 |
| 3 | Comparative 3 | 10 | 400 | 10.0 | 350 | 100 |

Example 11

A device having the structure shown in FIG. 3 was prepared.

In the same manner as in Example 1, a hole-transporting layer 5 was formed on the transparent conductive support substrate.

Further, a luminescent layer 3 was formed by forming a film of 20 nm in thickness from a spiro compound represented by the exemplified compound No. 3 by a vacuum evaporation method. The film formation was performed under the conditions in which the degree of vacuum at the time of evaporation was $1.0 \times 10^{-4}$ Pa and the film formation rate was 0.2 to 0.3 nm/sec.

Furthermore, an electron-transporting layer 6 was formed by forming a film of 40 nm in thickness from aluminum tris quinolinol by a vacuum evaporation method. The film formation was performed under the conditions in which the degree of vacuum at the time of evaporation was $1.0 \times 10^{-4}$ Pa and the film formation rate was 0.2 to 0.3 nm/sec.

Next, after forming a cathode 4 in the same manner as in Example 1, the resulting product was sealed.

When a direct current voltage of 8 V was applied on the device obtained in this way with an ITO electrode (anode 2) provided as a positive electrode and an Al—Li electrode (cathode 4) provided as a negative electrode, the current was caused to flow into the device at a current density of 12.0 MA/cm$^2$ and blue-colored luminescence at a luminance of 6700 cd/m$^2$ was observed.

Furthermore, when the current density was kept at 10.0 mA/cm$^2$ and the voltage was applied for 100 hours, an initial luminance of 5500 cd/m$^2$ changed to a luminance of 5200 cd/m$^2$ after 100 hours, indicating small deterioration of luminance.

Examples 12 to 20

Devices were prepared and evaluated in the same way as that of Example 11, except that the exemplified compounds shown in Table 2 were used in place of the exemplified compound No. 3. The results are shown in Table 2.

Comparative Examples 4 to 6

Devices were prepared and evaluated in the same way as that of Example 11, except that the comparative compounds No. 1 to No. 3 were used in place of the exemplified compound No. 3. The results are shown in Table 2.

Example 21

A device having the structure shown in FIG. 3 was prepared.

On a transparent conductive support substrate similar to that in Example 1, a chloroform solution of a compound represented by the following structural formula was applied into a film of 20 nm in thickness by a spin-coating method, resulting in a hole-transporting layer 5.

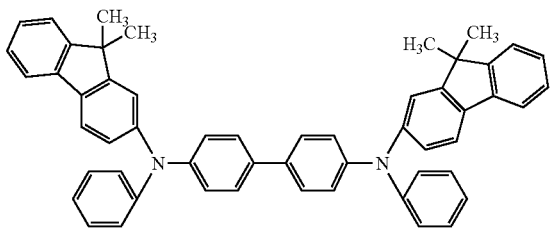

Furthermore, the spiro compound represented as the exemplified compound No. 7 and the fluorene compound represented as the exemplified compound No. FL-1 (weight ratio of 100:1) were deposited into a film with a thickness of 20 nm by the vacuum evaporation method to form a luminescent layer 3. The film formation was performed under the conditions in which the degree of vacuum at the time of evaporation was $1.0 \times 10^{-4}$ Pa and the film formation rate was 0.2 to 0.3 nm/sec.

Furthermore, an electron-transporting layer 6 was formed by forming a film of 40 nm in thickness from aluminum tris quinolinol by a vacuum evaporation method. The film formation was performed under the conditions in which the degree of vacuum at the time of evaporation was $1.0 \times 10^{-4}$ Pa and the film formation rate was 0.2 to 0.3 nm/sec.

Next, after forming a cathode 4 in the same manner as in Example 1, the resulting product was sealed.

When a direct current voltage of 8 V was applied on the device obtained in this way with an ITO electrode (anode 2) provided as a positive electrode and an Al—Li electrode

TABLE 2

| | | Initial stage | | Durability | | |
|---|---|---|---|---|---|---|
| Example No. | Exemplified compound No. | Applied voltage (V) | Luminance (cd/m$^2$) | Current density (mA/cm$^2$) | Initial luminance (cd/m$^2$) | Luminance after 100-hour (cd/m$^2$) |
| Example 11 | 3 | 8 | 6700 | 10.0 | 5500 | 5200 |
| 12 | 6 | 8 | 6500 | 10.0 | 5200 | 4800 |
| 13 | 8 | 8 | 7300 | 10.0 | 6000 | 5700 |
| 14 | 11 | 8 | 5200 | 10.0 | 4400 | 4100 |
| 15 | 15 | 8 | 3900 | 10.0 | 3600 | 3400 |
| 16 | 19 | 8 | 5100 | 10.0 | 4200 | 4000 |
| 17 | 23 | 8 | 5600 | 10.0 | 4600 | 4300 |
| 18 | 25 | 8 | 3600 | 10.0 | 2700 | 2500 |
| 19 | 26 | 8 | 3800 | 10.0 | 2900 | 2600 |
| 20 | 28 | 8 | 5200 | 10.0 | 4100 | 3800 |
| Comparative Example 4 | Comparative 1 | 8 | 800 | 10.0 | 770 | 450 |
| 5 | Comparative 2 | 8 | 500 | 10.0 | 400 | 150 |
| 6 | Comparative 3 | 8 | 1200 | 10.0 | 900 | 300 |

(cathode 4) provided as a negative electrode, the current was caused to flow into the device at a current density of 13.5 mA/cm² and blue-colored luminescence at a luminance of 16000 cd/m² was observed.

Furthermore, when the current density was kept at 10.0 mA/cm² and the voltage was applied for 100 hours, the initial luminance of 12000 cd/m² changed to a luminance of 9000 cd/m² after 100 hours, indicating small deterioration of luminance.

Examples 22 to 53

Devices were prepared and evaluated in the same way as that of Example 21, except that the exemplified fluorene compound shown in Table 3 was used in place of the exemplified fluorene compound No. FL-1. The results are shown in Table 3.

Comparative Examples 7 to 9

Devices were prepared and evaluated in the same way as that of Example 21, except that the comparative compounds No. 1 to No. 3 were used in place of the exemplified compound No. 7. The results are shown in Table 3.

Example 54

A device having the structure shown in FIG. 3 was prepared.

On a transparent conductive support substrate similar to that in Example 1, a chloroform solution of a compound represented by the following structural formula was applied into a film of 20 nm in thickness by a spin-coating method, resulting in a hole-transporting layer 5.

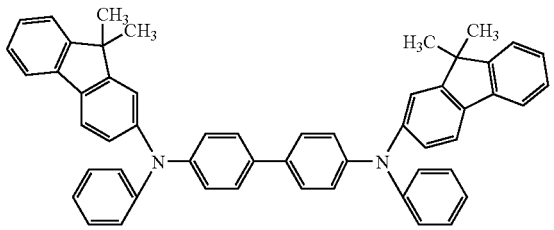

TABLE 3

| Example No. | Exemplified compound No. | Exemplified fluorene compound No. | Initial stage | | Durability | | |
| --- | --- | --- | --- | --- | --- | --- | --- |
| | | | Applied voltage (V) | Luminance (cd/m²) | Current density (mA/cm²) | Initial luminance (cd/m²) | Luminance after 100-hour (cd/m²) |
| Example 21 | 7 | FL-1 | 8 | 16000 | 10.0 | 12000 | 9000 |
| 22 | 7 | FL-2 | 8 | 15000 | 10.0 | 12000 | 8000 |
| 23 | 7 | FL-3 | 8 | 17000 | 10.0 | 14000 | 10000 |
| 24 | 7 | FL-4 | 8 | 12000 | 10.0 | 8500 | 7000 |
| 25 | 7 | FL-5 | 8 | 9000 | 10.0 | 7000 | 6000 |
| 26 | 7 | FL-6 | 8 | 19000 | 10.0 | 14000 | 11000 |
| 27 | 7 | FL-7 | 8 | 20000 | 10.0 | 14000 | 12000 |
| 28 | 7 | FL-9 | 8 | 22000 | 10.0 | 17000 | 13000 |
| 29 | 7 | FL-10 | 8 | 21000 | 10.0 | 16000 | 13000 |
| 30 | 7 | FL-12 | 8 | 17000 | 10.0 | 11000 | 8500 |
| 31 | 7 | FL-13 | 8 | 13000 | 10.0 | 10000 | 7000 |
| 32 | 7 | FL-14 | 8 | 18000 | 10.0 | 16000 | 14000 |
| 33 | 7 | FL-15 | 8 | 19000 | 10.0 | 16000 | 14000 |
| 34 | 7 | FL-18 | 8 | 19000 | 10.0 | 17000 | 15000 |
| 35 | 7 | FL-21 | 8 | 23000 | 10.0 | 19000 | 16000 |
| 36 | 7 | FL-24 | 8 | 24000 | 10.0 | 19000 | 17000 |
| 37 | 7 | FL-26 | 8 | 9500 | 10.0 | 8000 | 6000 |
| 38 | 7 | FL-27 | 8 | 17000 | 10.0 | 13000 | 11000 |
| 39 | 7 | FL-28 | 8 | 10000 | 10.0 | 8000 | 6500 |
| 40 | 7 | FL-29 | 8 | 8000 | 10.0 | 7000 | 6000 |
| 41 | 7 | FL-30 | 8 | 9500 | 10.0 | 8000 | 6500 |
| 42 | 7 | FL-31 | 8 | 12000 | 10.0 | 10000 | 7000 |
| 43 | 7 | FL-32 | 8 | 23000 | 10.0 | 18000 | 15000 |
| 44 | 7 | FL-33 | 8 | 23000 | 10.0 | 17000 | 14000 |
| 45 | 7 | FL-36 | 8 | 25000 | 10.0 | 19000 | 16000 |
| 46 | 7 | FL-37 | 8 | 25000 | 10.0 | 18000 | 15000 |
| 47 | 7 | FL-38 | 8 | 20000 | 10.0 | 17000 | 14000 |
| 48 | 7 | FL-39 | 8 | 24000 | 10.0 | 19000 | 16000 |
| 49 | 7 | FL-41 | 8 | 26000 | 10.0 | 20000 | 16000 |
| 50 | 7 | FL-42 | 8 | 26000 | 10.0 | 21000 | 17000 |
| 51 | 7 | FL-44 | 8 | 15000 | 10.0 | 12000 | 9500 |
| 52 | 7 | FL-45 | 8 | 12000 | 10.0 | 9000 | 7500 |
| 53 | 7 | FL-46 | 8 | 13000 | 10.0 | 11000 | 7000 |
| Comparative Example 7 | Comparative 1 | FL-1 | 8 | 3000 | 10.0 | 2500 | 900 |
| 8 | Comparative 2 | FL-1 | 8 | 2000 | 10.0 | 1500 | 200 |
| 9 | Comparative 3 | FL-1 | 8 | 4500 | 10.0 | 3500 | 600 |

Furthermore, the spiro compound represented as the exemplified compound No. 2 and a compound represented by the following structural formula (weight ratio of 100:5) were deposited into a film with a thickness of 20 nm by the vacuum evaporation method to form a luminescent layer 3. The film formation was performed under the conditions in which the degree of vacuum at the time of evaporation was $1.0 \times 10^{-4}$ Pa and the film formation rate was 0.2 to 0.3 nm/sec.

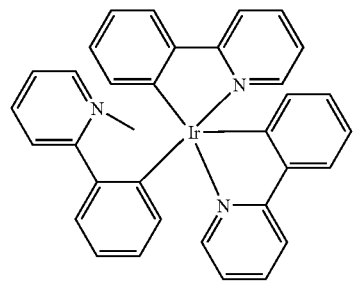

Furthermore, an electron-transporting layer 6 was formed by forming a film of 40 nm in thickness from bathophenanthroline (BPhen) by the vacuum evaporation method. The film formation was performed under the conditions in which the degree of vacuum at the time of evaporation was $1.0 \times 10^{-4}$ Pa and the film formation rate was 0.2 to 0.3 nm/sec.

Next, after forming a cathode 4 in the same manner as in Example 1, the resulting product was sealed.

When a direct current voltage of 8 V was applied on the device obtained in this way with an ITO electrode (anode 2) provided as a positive electrode and an Al—Li electrode (cathode 4) provided as a negative electrode, the current was caused to flow into the device at a current density of 10.5 mA/cm$^2$ and green-colored luminescence at a luminance of 9000 cd/m$^2$ was observed.

Furthermore, when the current density was kept at 7.0 mA/cm$^2$ and the voltage was applied for 100 hours, the initial luminance of 7500 cd/m$^2$ changed to a luminance of 6500 cd/m$^2$ after 100 hours, indicating small deterioration of luminance.

Examples 55 to 63

Devices were prepared and evaluated in the same way as that of Example 54, except that the exemplified compound shown in Table 4 was used in place of the exemplified compound No. 2. The results are shown in Table 4.

Comparative Examples 10 to 12

Devices were prepared and evaluated in the same way as that of Example 54, except that the comparative compounds No. 1 to No. 3 were used in place of the exemplified compound No. 2. The results are shown in Table 4.

TABLE 4

| | | Initial stage | | Durability | | |
| --- | --- | --- | --- | --- | --- | --- |
| Example No. | Exemplified compound No. | Applied voltage (V) | Luminance (cd/m$^2$) | Current density (mA/cm$^2$) | Initial luminance (cd/m$^2$) | Luminance after 100-hour (cd/m$^2$) |
| Example 54 | 2 | 8 | 9000 | 7.0 | 7500 | 6500 |
| 55 | 4 | 8 | 9500 | 7.0 | 8000 | 6500 |
| 56 | 6 | 8 | 7000 | 7.0 | 6000 | 5000 |
| 57 | 12 | 8 | 8000 | 7.0 | 6000 | 5500 |
| 58 | 14 | 8 | 14000 | 7.0 | 11000 | 9000 |
| 59 | 15 | 8 | 10000 | 7.0 | 9000 | 7500 |
| 60 | 20 | 8 | 10000 | 7.0 | 8000 | 7000 |
| 61 | 22 | 8 | 9500 | 7.0 | 8000 | 7500 |
| 62 | 29 | 8 | 15000 | 7.0 | 13000 | 10000 |
| 63 | 30 | 8 | 8500 | 7.0 | 8000 | 7000 |
| Comparative Example 10 | Comparative 1 | 8 | 1300 | 7.0 | 900 | 300 |
| 11 | Comparative 2 | 8 | 1000 | 7.0 | 900 | 100 |
| 12 | Comparative 3 | 8 | 2500 | 7.0 | 2000 | 700 |

Example 64

A device having the structure shown in FIG. 1 was prepared.

On a transparent conductive support substrate which was similar to that of Example 1, a solution prepared by dissolving 0.050 g of a spiro compound represented by the exemplified compound No. 1 and 1.00 g of poly-N-vinyl carbazole (a weight average molecular weight=63,000) in 80 ml of chloroform was applied into a film of 120 nm in thickness by a spin-coating method (rotation speed=2000 rpm) to form an organic layer (a luminescent layer 3).

Next, after forming a cathode 4 in the same manner as in Example 1, the resulting product was sealed.

When a direct current voltage of 10 V was applied on the device obtained in this way with an ITO electrode (anode 2) provided as a positive electrode and an Al—Li electrode (cathode 4) provided as a negative electrode, the current was caused to flow into the device at a current density of 8.0 mA/cm² and blue-colored luminescence at a luminance of 1900 cd/m² was observed.

Furthermore, when the current density was kept at 5.0 mA/cm² and the voltage was applied for 100 hours in the nitrogen atmosphere, the initial luminance of 1000 cd/m² changed to a luminance of 850 cd/m² after 100 hours, indicating small deterioration of luminance.

Examples 65 to 68

Devices were prepared and evaluated in the same way as that of Example 64, except that the exemplified compound shown in Table 5 was used in place of the exemplified compound No. 1. The results are shown in Table 5.

Comparative Examples 13 to 15

Devices were prepared and evaluated in the same way as that of Example 64, except that the comparative compounds No. 1 to No. 3 were used in place of the exemplified compound No. 1. The results are shown in Table 5.

TABLE 5

| | | Initial stage | | Durability | | |
|---|---|---|---|---|---|---|
| Example No. | Exemplified compound No. | Applied voltage (V) | Luminance (cd/m²) | Current density (mA/cm²) | Initial luminance (cd/m²) | Luminance after 100-hour (cd/m²) |
| Example 64 | 1 | 10 | 1900 | 5.0 | 1000 | 850 |
| 65 | 7 | 10 | 2500 | 5.0 | 1600 | 1400 |
| 66 | 19 | 10 | 1400 | 5.0 | 1000 | 800 |
| 67 | 20 | 10 | 1800 | 5.0 | 1400 | 1300 |
| 68 | 24 | 10 | 1900 | 5.0 | 1200 | 950 |
| Comparative Example 13 | Comparative 1 | 10 | 300 | 5.0 | 200 | No luminescence |
| 14 | Comparative 2 | 10 | 200 | 5.0 | 150 | No luminescence |
| 15 | Comparative 3 | 10 | 550 | 5.0 | 400 | 50 |

As described with reference to the embodiments and the examples, the organic luminescence device using the spiro compound represented by the general formula [I] or the general formula [II] provides luminescence with a high luminance by the application of a low voltage and is excellent in durability.

In particular, the organic layer containing the spiro compound of the present invention is excellent as an electron-transporting layer and is also excellent as a luminescent layer.

Furthermore, the device can be prepared by using a vacuum evaporation method or a casting method, so that the device having a large area can be easily prepared at a comparatively low cost.

What is claimed is:
1. An organic luminescence device comprising at least a pair of electrodes including an anode and a cathode and one or a plurality of layers containing an organic compound sandwiched between the pair of electrodes, wherein at least one of the layers containing the organic compound contains at least one spiro compound represented by the following general formula [II]:

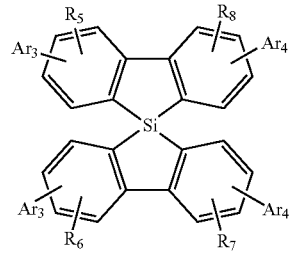

wherein $R_5$, $R_6$, $R_7$, and $R_8$ represent a hydrogen atom, a substituted or unsubstituted alkyl group, a substituted or unsubstituted aralkyl group, a substituted or unsubstituted aryl group, a substituted or unsubstituted heterocyclic group, a substituted amino group, cyano group, or a halogen atom, and $R_5$, $R_6$, $R_7$, and $R_8$, may be identical or different from each other; and $Ar_3$ and $Ar_4$ represent a substituted or unsubstituted condensed polycyclic aromatic group or a substituted or unsubstituted condensed polycyclic heterocyclic group, which may be identical or different from each other and wherein at least one of $Ar_3$ and $Ar_4$ is a condensed polycyclic aromatic group represented by one of the following general formula [III] to [VIII]:

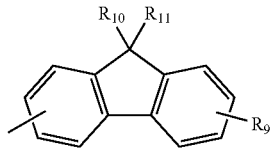

wherein $R_9$ represents a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom; and $R_{10}$ and $R_{11}$ represent a hydrogen atom, a substituted or unsubstituted alkyl group, a substituted or unsubstituted aralkyl group, a substituted or unsubstituted aryl group, or a substituted or unsubstituted heterocyclic group, which may be identical or different from each other;

[IV]

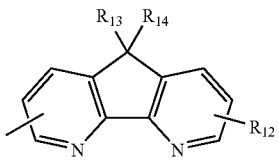

wherein $R_{12}$ represents a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom; and $R_{13}$ and $R_{14}$ represent a hydrogen atom, a substituted or unsubstituted alkyl group, a substituted or unsubstituted aralkyl group, a substituted or unsubstituted aryl group, or a substituted or unsubstituted heterocyclic group, which may be identical or different from each other; and

[V]

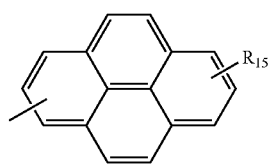

[VI]

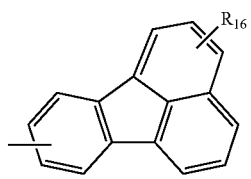

[VII]

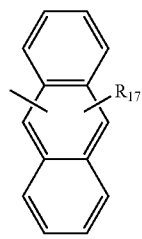

[VIII]

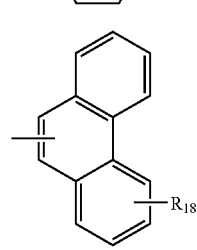

[IX]

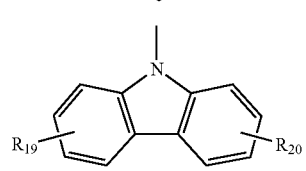

wherein $R_{15}$ to $R_{18}$ represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom; and wherein at least a luminescent layer among the layers containing the organic compound contains at least one of the spiro compounds and a fluorene compound represented by the following general formula [X]:

[X]

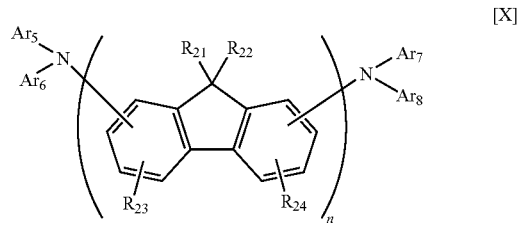

wherein $R_{21}$ and $R_{22}$ represent a hydrogen atom, a substituted or unsubstituted alkyl group, a substituted or unsubstituted aralkyl group, a substituted or unsubstituted aryl group, or a substituted or unsubstituted heterocyclic group, $R_{21}$ themselves or $R_{22}$ themselves, which are bonded to different fluorene groups, may be identical or different from each other, and $R_{21}$ and $R_{22}$ that are bonded to the same fluorene group may be identical or different from each other; $R_{23}$ and $R_{24}$ represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen atom, and $R_{23}$ themselves or $R_{24}$ themselves, which are bonded to different fluorene groups, may be identical or different from each other, and $R_{23}$ and $R_{24}$ that are bonded to the same fluorene group may be identical or different from each other; $Ar_5$, $Ar_6$, $Ar_7$, and $Ar_8$ represent a substituted or unsubstituted aromatic group, a substituted or unsubstituted heterocyclic group, a substituted or unsubstituted condensed polycyclic aromatic group, or a substituted or unsubstituted condensed polycyclic heterocyclic group, which may be identical or different from each other, and $Ar_5$ and $Ar_6$ as well as $Ar_7$ and $Ar_8$ may be bonded with each other to form rings, respectively; and n represents an integral number of 1 to 10.

2. An organic luminescence device comprising at least a pair of electrodes including an anode and a cathode and one or a plurality of layers containing an organic compound sandwiched between the pair of electrodes, wherein at least one of the layers containing the organic compound contains at least one spiro compound represented by the following general formula [II]:

[II]

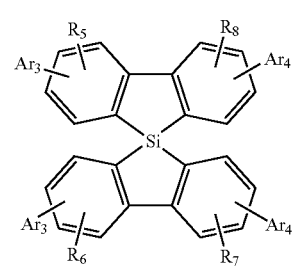

wherein $R_5$, $R_6$, $R_7$, and $R_8$ represent a hydrogen atom, a substituted or unsubstituted alkyl group, a substituted or unsubstituted aralkyl group, a substituted or unsubstituted aryl group, a substituted or unsubstituted heterocyclic group, a substituted amino group, cyano group, or a halogen atom, and $R_5$, $R_6$, $R_7$, and $R_8$ may be identical or different from each other; and $Ar_3$ and $Ar_4$ represent a substituted or unsubstituted condensed polycyclic aromatic group or a substituted or unsubstituted condensed polycyclic heterocyclic group, which may be identical or different from each other and wherein at least one of $Ar_3$ and $Ar_4$ is a condensed polycyclic aromatic group represented by one of the following general formula [III] to [VIII]:

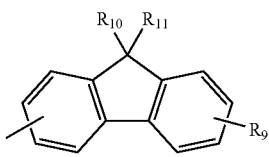

[III]

wherein $R_9$ represents a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom; and $R_{10}$ and $R_{11}$ represent a hydrogen atom, a substituted or unsubstituted alkyl group, a substituted or unsubstituted aralkyl group, a substituted or unsubstituted aryl group, or a substituted or unsubstituted heterocyclic group, which may be identical or different from each other;

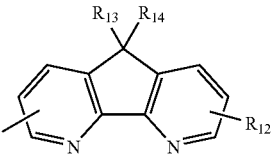

[IV]

wherein $R_{12}$ represents a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom; and $R_{13}$ and $R_{14}$ represent a hydrogen atom, a substituted or unsubstituted alkyl group, a substituted or unsubstituted aralkyl group, a substituted or unsubstituted aryl group, or a substituted or unsubstituted heterocyclic group, which may be identical or different from each other; and

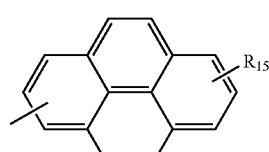

[V]

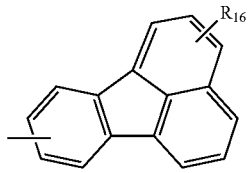

[VI]

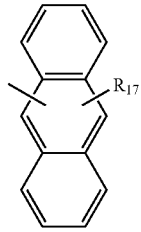

[VII]

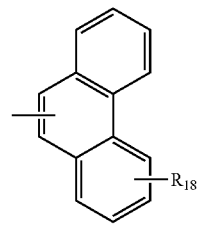

[VIII]

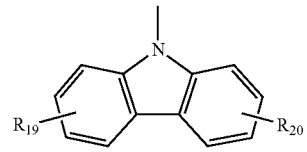

[IX]

wherein $R_{15}$ to $R_{18}$ represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom; and wherein at least a luminescent layer among the layers containing the organic compound contains at least one of the spiro compounds and a fluorene compound represented by the following general formula [XI]:

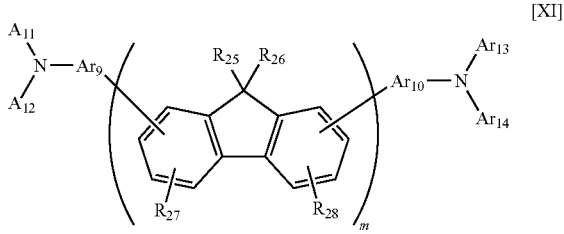

[XI]

(wherein $R_{25}$ and $R_{26}$ represent a hydrogen atom, a substituted or unsubstituted alkyl group, a substituted or unsubstituted aralkyl group, a substituted or unsubstituted aryl group, or a substituted or unsubstituted heterocyclic group, $R_{25}$ themselves or $R_{26}$ themselves, which are bonded to different fluorene groups, may be identical or different from each other, and $R_{25}$ and $R_{26}$ that are bonded to the same fluorene group may be identical or different from each other; $R_{27}$ and $R_{28}$ represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen atom, and $R_{27}$ themselves or $R_{28}$ themselves, which are bonded to different fluorene groups, may be identical or different from each other, and $R_{27}$ and $R_{28}$ that are bonded to the same fluorene group may be identical or different from each other; $Ar_9$ and $Ar_{10}$ represent a substituted or unsubstituted divalent aromatic group or a substituted or unsubstituted divalent heterocyclic group, which may be identical or different from each other; $Ar_{11}$, $Ar_{12}$, $Ar_{13}$, and $Ar_{14}$ represent a substituted or unsubstituted aromatic group, a substituted or unsubstituted heterocyclic group, a substituted or unsubstituted condensed polycyclic aromatic group, or a substituted or unsubstituted condensed polycyclic heterocyclic group, which may be identical or different from each other, and $Ar_{11}$ and $Ar_{12}$ as well as $Ar_{13}$ and $Ar_{14}$ may be bonded with each other to form rings, respecdvely; and m represents an integral number of 1 to 10.)

\* \* \* \* \*